(12) United States Patent
Scheiner et al.

(10) Patent No.: US 12,415,075 B2
(45) Date of Patent: Sep. 16, 2025

(54) INTEGRATED SLEEP APNEA AND AT LEAST ONE OF CARDIAC MONITORING AND CARDIAC THERAPY

(71) Applicant: Medtronic, Inc., Minneapolis, MN (US)

(72) Inventors: Avram Scheiner, Vadnais Heights, MN (US); Randal C. Schulhauser, Phoenix, AZ (US); Becky L. Dolan, Chisago, MN (US)

(73) Assignee: Medtronic, Inc., Minneapolis, MN (US)

( * ) Notice: Subject to any disclaimer, the term of this patent is extended or adjusted under 35 U.S.C. 154(b) by 284 days.

(21) Appl. No.: 18/068,932

(22) Filed: Dec. 20, 2022

(65) Prior Publication Data

US 2023/0241391 A1 Aug. 3, 2023

Related U.S. Application Data

(60) Provisional application No. 63/306,367, filed on Feb. 3, 2022.

(51) Int. Cl.
*A61N 1/36* (2006.01)
*A61N 1/365* (2006.01)
*A61N 1/372* (2006.01)

(52) U.S. Cl.
CPC ........ *A61N 1/3611* (2013.01); *A61N 1/36139* (2013.01); *A61N 1/36514* (2013.01); *A61N 1/37235* (2013.01)

(58) Field of Classification Search
CPC .............. A61N 1/3611; A61N 1/36139; A61N 1/36514; A61B 5/0205; A61B 5/4836; A61B 5/686
See application file for complete search history.

(56) References Cited

U.S. PATENT DOCUMENTS 6,076,015 A * 6/2000 Hartley .............. A61N 1/36521
607/20
7,094,207 B1 8/2006 Koh
(Continued)

FOREIGN PATENT DOCUMENTS

EP 3071288 B1 11/2018

OTHER PUBLICATIONS

Extended Search Report from counterpart European Application No. 23152476.0 dated Jun. 5, 2023, 7 pp.
(Continued)

*Primary Examiner* — Paula J Stice
(74) *Attorney, Agent, or Firm* — Shumaker & Sieffert, P.A.

(57) ABSTRACT

An implantable medical device (IMD) includes therapy delivery circuitry, sensing circuitry, and processing circuitry. The processing circuitry is configured to determine one or more sleep apnea therapy parameters, control the therapy delivery circuitry to deliver sleep apnea therapy via a first set of electrodes implantable within the patient in accordance with the one or more sleep apnea therapy parameters, and at least one of: (1) monitor a cardiac signal sensed with the sensing circuitry, or (2) determine one or more cardiac therapy parameters, and control the therapy delivery circuitry to deliver cardiac therapy via a second set of electrodes implantable within the patient in accordance with the one or more cardiac therapy parameters.

14 Claims, 5 Drawing Sheets

(56) References Cited

U.S. PATENT DOCUMENTS

| | | |
|---|---|---|
| 9,757,560 B2 | 9/2017 | Papay |
| 10,029,098 B2 | 7/2018 | Papay |
| 10,065,038 B2 | 9/2018 | Papay |
| 10,744,339 B2 | 8/2020 | Makansi |
| 2009/0078274 A1 | 3/2009 | Bhat et al. |
| 2011/0196254 A1 | 8/2011 | Wenzel et al. |
| 2012/0029362 A1* | 2/2012 | Patangay .............. A61B 5/4818 607/42 |
| 2015/0283383 A1 | 10/2015 | Ternes et al. |
| 2017/0290528 A1 | 10/2017 | Ternes et al. |
| 2020/0269044 A1 | 8/2020 | Papay |
| 2020/0282213 A1* | 9/2020 | Tesfayesus ........... A61B 5/4561 |
| 2020/0338358 A1 | 10/2020 | Makansi |
| 2020/0346017 A1 | 11/2020 | Caparso et al. |

OTHER PUBLICATIONS

Response to Extended Search Report dated Jun. 5, 2023, from counterpart European Application No. 23152476.0 filed Jan. 30, 2024, 19 pp.

Murtaza et al., "Pacing therapies for sleep apnea and cardiovascular outcomes: A systematic review", Journal of Interventional Cardiac Electrophysiology, vol. 61, May 22, 2020, p. 11-17.

* cited by examiner

INTEGRATED SLEEP APNEA AND AT LEAST ONE OF CARDIAC MONITORING AND CARDIAC THERAPY

This application claims the benefit of U.S. Provisional Patent Application 63/306,367, which was filed on Feb. 3, 2022, the entire content of which is incorporated herein by reference.

TECHNICAL FIELD

This disclosure relates to techniques for delivery of electrical stimulation signal for therapy.

BACKGROUND

Obstructive sleep apnea (OSA), central sleep apnea (CSA), mixed apnea (combination of both OSA and CSA), and upper airway restrictive/resistance syndrome (UARS) are examples of sleep apneas that obstruct the airway, and cause lack of adequate levels of oxygen during sleep. Lack of adequate levels of oxygen during sleep can contribute to abnormal heart rhythms, heart attack, heart failure, high blood pressure, stroke, seizures, memory problems, and increased accidents during the day due to inadequate sleep. Additionally, loss of sleep occurs when a person is awakened during an apneic episode.

SUMMARY

The techniques of this disclosure generally relate to techniques for a single implantable medical device (IMD) configured to deliver sleep apnea therapy and at least one of deliver cardiac therapy and monitor a cardiac signal. That is, one, unitary IMD may include circuitry that is configured to deliver electrical stimulation therapy for treating sleep apnea, and circuitry that is configured to deliver electrical stimulation therapy for treating one or more cardiac conditions. In some examples, in addition to or instead of delivering electrical stimulation therapy for treating one or more cardiac conditions, the unitary IMD may include circuitry to monitor a cardiac signal sensed with sensing circuitry of the IMD. That is, the IMD that delivers sleep apnea therapy may also include circuitry for monitoring a cardiac signal.

In one or more examples, a patient with sleep apnea may also have other conditions, such as cardiac conditions. In this way, rather than having multiple surgeries for implanting different medical devices for treating sleep apnea and cardiac conditions, fewer surgeries may be needed to implant the one IMD for treating both sleep apnea and cardiac conditions. Similarly, even if treatment for cardiac conditions is not needed, the patient may be implanted with a device that monitors cardiac signals, and this same device can be used to deliver therapy for sleep apnea. Moreover, because the single IMD is configured to deliver sleep apnea therapy and cardiac therapy and/or monitor cardiac signals, the single IMD may be configured to utilize patient condition information used for delivering sleep apnea therapy to inform cardiac therapy, or vice-versa. Utilizing patient condition information used for delivering sleep apnea therapy to inform cardiac therapy, or vice-versa may be difficult or unavailable if multiple devices are utilized to separately provide sleep apnea therapy and cardiac therapy.

In one example, the disclosure describes an implantable medical device (IMD), the IMD comprising: therapy delivery circuitry; sensing circuitry; and processing circuitry configured to: determine one or more sleep apnea therapy parameters; control the therapy delivery circuitry to deliver sleep apnea therapy via a first set of electrodes implantable within the patient in accordance with the one or more sleep apnea therapy parameters; and at least one of: (1) monitor a cardiac signal sensed with the sensing circuitry; or (2) determine one or more cardiac therapy parameters, and control the therapy delivery circuitry to deliver cardiac therapy via a second set of electrodes implantable within the patient in accordance with the one or more cardiac therapy parameters.

In one example, the disclosure describes a method of controlling therapy, the method comprising: determining one or more sleep apnea therapy parameters; controlling a therapy delivery circuitry to deliver sleep apnea therapy via a first set of electrodes implantable within a patient in accordance with the one or more sleep apnea therapy parameters; and at least one of: (1) monitoring a cardiac signal sensed with sensing circuitry; or (2) determining one or more cardiac therapy parameters, and controlling the therapy delivery circuitry to deliver cardiac therapy via a second set of electrodes implantable within the patient in accordance with the one or more cardiac therapy parameters.

In one example, the disclosure describes a computer-readable storage medium storing instructions thereon that when executed cause one or more processors to: determine one or more sleep apnea therapy parameters; control a therapy delivery circuitry to deliver sleep apnea therapy via a first set of electrodes implantable within a patient in accordance with the one or more sleep apnea therapy parameters; and at least one of: (1) monitor a cardiac signal sensed with sensing circuitry; or (2) determine one or more cardiac therapy parameters, and control the therapy delivery circuitry to deliver cardiac therapy via a second set of electrodes implantable within the patient in accordance with the one or more cardiac therapy parameters.

The details of one or more examples of the disclosure are set forth in the accompanying drawings and the description below. Other features, objects, and advantages of the techniques described in this disclosure will be apparent from the description and drawings, and from the claims.

DETAILED DESCRIPTION

Figure 1:
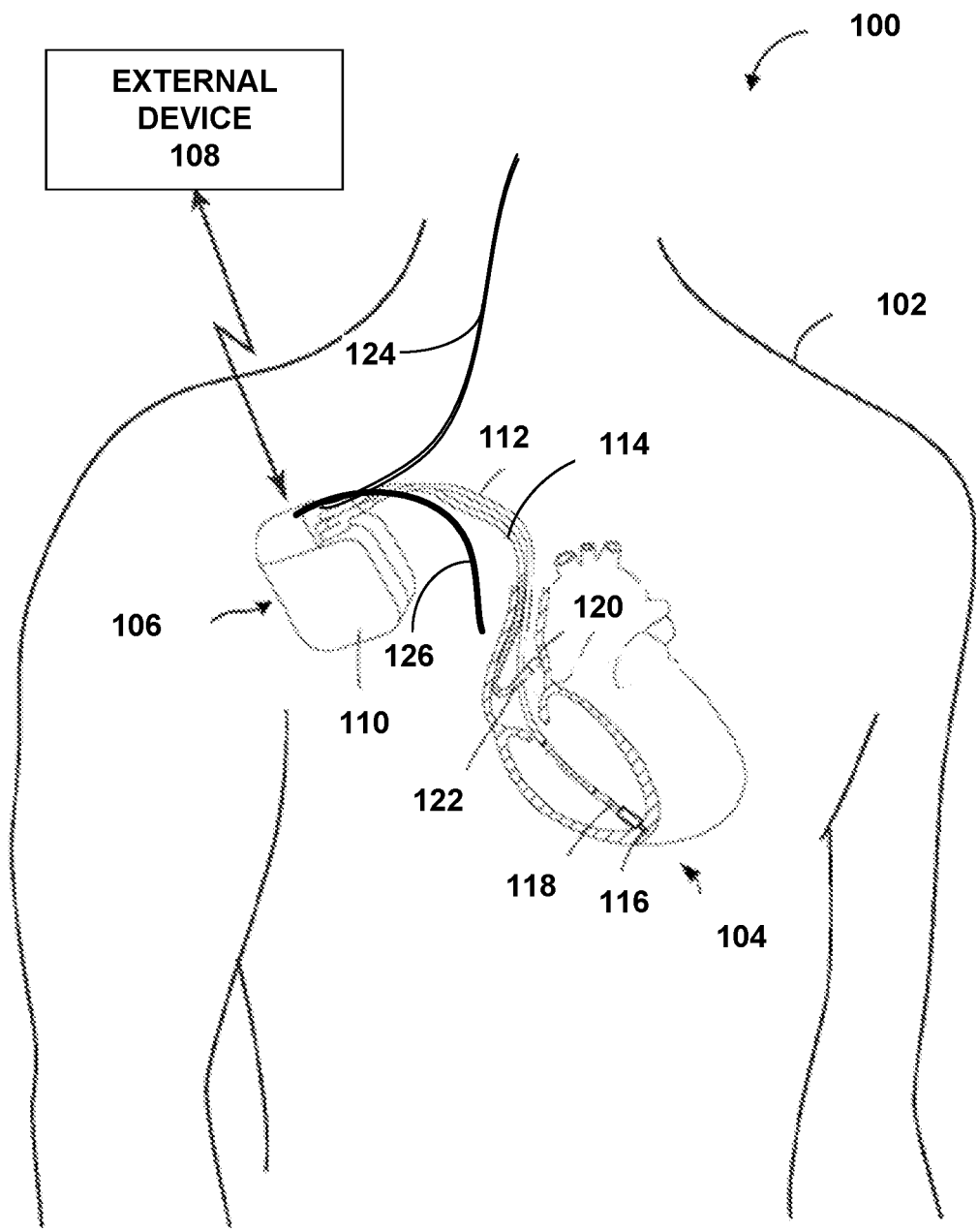
FIG. 1 is a conceptual diagram of an implantable medical device (IMD) system for delivering sleep apnea therapy and at least one of cardiac signal monitoring and cardiac therapy.

This disclosure describes examples of an integrated cardiac therapy and sleep apnea therapy delivery device, such that a single implantable medical device (IMD) (e.g., single implantable housing) is utilized to provide sleep apnea therapy and at least one of cardiac therapy or monitoring of cardiac signals. That is, a single IMD may be configured to deliver sleep apnea therapy and cardiac therapy, deliver sleep apnea therapy and monitor cardiac signals, and/or deliver sleep apnea therapy, monitor cardiac signals, and deliver cardiac therapy.

Many patients experience multiple co-morbidities. For instance, patients with sleep apnea may tend to also experience one or more cardiac conditions. In some estimates, 76% of heart failure patients, 59% of pacemaker patients, and 49% of patients with atrial fibrillation have sleep apnea.

In some cases, the sleep apnea may partially cause a cardiac condition. For example, sleep apnea is a breathing disorder that cuts oxygen supply to various systems and organs of the body. To deal with the reduction in oxygenation levels, organs and systems of the body may trigger one or more compensatory mechanisms. With respect to the cardiovascular system, the compensatory mechanism(s) cause the heart to increase blood output for a period of time. As such, the cardiac compensatory mechanisms cause increased exertion of the heart. Moreover, at the end of a sleep apnea episode and during a recovery period that follows a sleep apnea episode, the patient's heart rate may increase significantly, due to alveolar hyperventilation caused by the pulmonary system's compensatory mechanisms. The heart rate spike after a sleep apnea episode may be greater in magnitude than naturally occurring heart rate increases that are exhibited by the normal phenomenon of cyclical variation of heart rate (CVHR). As such, both the reduced oxygen supply during a sleep apnea episode and the hyperventilation that follows a sleep apnea episode may cause exertion levels in the heart that exceed normal levels of heart exertion.

The abnormal oxygenation conditions associated with sleep apnea may affect various systems and vital organs adversely. Repeated instances of increased heart exertion, as may be caused by frequent compensatory blood output to counter chronic sleep apnea and by increasing the heart rate to accommodate subsequent hyperventilation, increases the likelihood of heart ailments or possible heart failure.

In accordance with one or more examples, the single IMD that provides both cardiac therapy and sleep apnea therapy may reduce the number of surgeries that a patient needs, and promote a way in which cardiac therapy and sleep apnea therapy can be used together. In some examples, the single IMD provides sleep apnea therapy and monitors cardiac signals. In some examples, the single IMD provides sleep apnea therapy, cardiac therapy, and monitors cardiac signals.

For instance, some patients having a cardiac condition may be implanted with a first medical device that addresses the cardiac condition or monitors the cardiac condition, and then later implanted with a second medical device that addresses sleep apnea. Implanting two stimulation devices to treat the sleep apnea and cardiac condition or monitor the cardiac condition may be burdensome on the patient, which may increase morbidity, medical risk, and cost. With the example techniques described in this disclosure, the single IMD may provide both cardiac therapy and sleep apnea therapy, provide cardiac signal monitoring and sleep apnea therapy, or provide cardiac signal monitoring, cardiac therapy, and sleep apnea therapy, which may not only reduce surgeries, but may also reduce potential electrical incompatibility issues and increase overall therapy effectiveness by coordinating therapy application.

For instance, the IMD may include therapy delivery circuitry and processing circuitry. The processing circuitry may be configured to determine one or more sleep apnea therapy parameters, control therapy delivery circuitry of the IMD to deliver sleep apnea therapy via a first set of electrodes implantable within the patient in accordance with the one or more sleep apnea therapy parameters. The processing circuitry may also be configured to at least one of: (1) monitor a cardiac signal sensed with the sensing circuitry, or (2) determine one or more cardiac therapy parameters, and control the therapy delivery circuitry to deliver cardiac therapy via a second set of electrodes implantable within the patient in accordance with the one or more cardiac therapy parameters.

In some examples, the processing circuitry may determine the cardiac therapy parameters in response to sensing a condition associated with the sleep apnea therapy parameters, or may determine the sleep apnea parameters based on the monitored cardiac signal. As an example, during sleep, the patient may experience an apneic episode, and the processing circuitry may change the sleep apnea therapy parameters (e.g., increase amplitude). There may potentially be an increased risk of arrythmia due to the apneic episode. In one or more examples, the processing circuitry may determine the cardiac therapy parameters based on the apneic episode.

As another example, if the processing circuitry determines that a change in the cardiac therapy parameters is appropriate, the processing circuitry may determine whether change in sleep apnea therapy parameters is appropriate. For instance, because the sleep apnea may negatively contribute to the effects of the cardiac condition, there may be more therapeutic gains by changing both the cardiac therapy parameters and the sleep apnea therapy parameters, than by changing just the cardiac therapy parameters. That is, more therapeutic efficacy may be achieved by changing both the cardiac therapy parameters and the sleep apnea therapy parameters, than only the cardiac therapy parameters or only the sleep apnea therapy parameters.

As another example, the processing circuitry may determine when and how often the patient experiences a cardiac condition based on the monitoring of the cardiac signal. The cause of the cardiac condition may be due to the sleep apnea. The processing circuitry may adjust the sleep apnea therapy parameters to reduce the instances of the cardiac condition. In some examples, the processing circuitry may determine the effectiveness of the sleep apnea therapy. For example, the processing circuitry may determine whether there is a reduction in the occurrence of the cardiac condition, and determine whether there is a correlation in the reduction in the occurrence of the cardiac condition. The processing circuitry may control the sleep apnea therapy based on whether there is correlation.

In some examples, rather than the processing circuitry of the IMD determining whether there is a reduction in occurrent of the cardiac condition, and whether there is correlation with the delivery of sleep apnea therapy, processing circuitry in some other device (e.g., in an external programmer, in a cloud computing environment, etc.) may determine whether there is a reduction in occurrent of the cardiac condition, and whether there is correlation with the delivery of sleep apnea therapy. The processing circuitry of the other device may then instruct the processing circuitry of the IMD to control the sleep apnea therapy based on the whether there is correlation.

In a cloud computing environment or with an external programmer, it may be possible to use not other measurements from the IMD, but other patient measurements to determine an overall health plan for the patient. For instance, the cloud computing environment may store information indicative of the patient blood pressure, medication the patient is taking, etc. The cloud computing environment may utilize the stored information, along with information from the IMD to present to a physician. The physician may evaluate the information to determine a therapeutic course of action.

By having a single IMD that provides sleep apnea therapy and cardiac therapy and/or cardiac signal monitoring (e.g., having cardiac therapy and/or sensing and sleep apnea therapy in a same housing that forms one device), coordinating sleep apnea and, potentially, cardiac therapy may be less processing intensive, as compared to having two different IMDs (e.g., medical devices in different housings) where one IMD in one housing provides cardiac therapy and the other IMD in another housing provides sleep apnea therapy.

FIG. 1 is a conceptual diagram of an implantable medical device (IMD) system for delivering sleep apnea therapy and at least one of cardiac signal monitoring and cardiac therapy. In the example of FIG. 1, medical device system 100 may include an implantable medical device (IMD) 106 and an external device 108. In accordance with one or more examples described in this disclosure, IMD 106 may be configured to provide sleep apnea therapy to patient 102 and at least one of cardiac signal monitoring and cardiac therapy to patient 102. Examples of the cardiac therapy include one or more of defibrillation therapy, cardiac resynchronization therapy (CRT), bradycardia therapy, and arrhythmia therapy. Examples of cardiac monitoring including monitoring cardiac signals for atrial tachyarrhythmias, heart failure, ventricular arrythmias, and the like. Another cardiovascular therapy may be carotid sinus stimulation. This therapy lowers blood pressure by stimulating the carotid sinus which vasodilates the blood vessels. Another cardiovascular therapy is cardiac potentiation therapy, which may be considered a subset of cardiac pacing. Cardiac potentiation therapy increases cardiac contractility by increasing sympathetic input to the heart by stimulating neural cardiac sympathetic fibers near the heart. Another cardiovascular therapy may be vagal nerve stimulation which decreases contractility and heart rate by stimulating the para-sympathetic drive to the heart by stimulating neural cardiac para-sympathetic fibers in the vagus nerve.

Examples of the sleep apnea therapy includes one or more of obstructive sleep apnea (OSA) therapy, central sleep apnea (CSA) therapy, and mixed apnea therapy (e.g., treating OSA and CSA simultaneously). Examples of the OSA therapy include anterior/posterior collapse therapy, and medial/lateral collapse therapy.

Accordingly, in some examples, IMD 106 may be considered as a combined cardiac and sleep apnea therapy device. For example, IMD 106 may be an implantable defibrillator with an OSA, CSA, or combined OSA/CSA device, an implantable CRT device with an OSA, CSA, or combined OSA/CSA device, an implantable CRT/defibrillator device with an OSA, CSA, or combined OSA/CSA device, or a bradycardia device with an OSA, CSA, or combined OSCA/CSA device. In some examples, IMD 106 may be considered as a combined sleep apnea therapy device and cardiac monitoring device. In some examples, IMD 106 may be considered as a combined cardiac and sleep apnea therapy device with cardiac monitoring.

IMD 106 may be capable of sensing and recording cardiac ventricular electrogram (EGM) signals from a position outside of heart 104. Sensing and recording cardiac ventricular EGM signals is one example of monitoring a cardiac signal sensed with sensing circuitry of IMD 106 In some examples, IMD 106 may include or be coupled to one or more additional sensors that generate one or more other physiological signals, such as signals that vary based on heart motion and/or sounds, blood pressure, blood flow, blood oxygenation, or respiration. Signals based on heart motion and/or sounds, blood pressure, blood flow, and blood oxygenation are additional examples of a cardia signal that is monitored with sensing circuitry of IMD 106. IMD 106 may be implantable submuscularly, such as in a pectoral location. In some examples, sensing respiration, and other pulmonary signals may be used for determining whether a patient has chronic obstructive pulmonary disease (COPD), and/or used to determine whether the therapy provided by IMD 106 assists a patient known to have COPD, or other pulmonary diseases.

Processing circuitry, sensing circuitry, stimulation circuitry (e.g., therapy delivery circuitry), and other circuitry configured for performing the techniques described herein may be housed within a sealed housing 110 of IMD 106. Housing 110 (or a portion thereof) may be conductive to serve as an electrode for pacing or sensing. In this way, IMD 106 forms a unitary device configured to deliver sleep apnea therapy and at least one of (including both) monitor a cardiac signal and deliver cardiac therapy.

External device 108 may be a computing device, e.g., used in a home, ambulatory, clinic, or hospital setting, to communicate with IMD 106 via wireless telemetry. External device 108 may be coupled to a remote patient monitoring system, such as CareLink®. CareLink® may be part of a cloud computing environment. In some examples, CareLink® may be used to further facilitate therapy delivery and monitoring. For instance, CareLink® may receive information sensed by IMD 106, and also include other information about patient 102 such as blood pressure information, medication information, allergy information, etc. A physician may utilize the information sensed by IMD 106 and presented via CareLink® to determine whether any changes to therapy are appropriate. Moreover, the physician may utilize CareLink® to determine whether any changes to medication, etc. are appropriate based on therapy delivered by IMD 106. In one or more examples, because IMD 106 is a single, unitary device that can provide cardiac and sleep apnea therapy, the physician may be able to update both cardiac and sleep apnea therapy with a single device, rather than program two different devices separately.

External device 108 may be, for example, a programmer, external monitor, or consumer device (e.g., smart phone), etc. External device 108 may be used to program commands or operating parameters into IMD 106 for controlling its functioning, e.g., when configured as a programmer for IMD 106. External device 108 may be used to interrogate IMD 106 to retrieve data, including device operational data as well as physiological data accumulated in memory. The interrogation may be automatic, e.g., according to a schedule, or in response to a remote or local user command. Programmers, external monitors, and consumer devices are examples of external devices 108 that may be used to interrogate IMD 106. Examples of communication techniques used by IMD 106 and external device 108 may include tissue conductance communication (TCC), or radiofrequency (RF) telemetry, which may be an RF link established via Bluetooth®, WiFi®, or medical implant communication service (MICS).

External device 108 may wirelessly communicate with IMD 106, e.g., to program the functionality of IMD 106, and to retrieve recorded physiological signals and/or patient parameter values or other data derived from such signals from the IMD 106. Both IMD 106 and external device 108 may include processing circuitry, and the processing circuitry of either device, of both devices, or any other device included in medical device system 100 may perform the techniques described herein, such as determining sleep apnea and/or cardiac therapy parameters.

Although not illustrated in the example of FIG. 1, a medical device system configured to implement the techniques described in this disclosure may include one or more implanted or external medical devices in addition to or instead of IMD 106. For example, a medical device system may include a vascular 1 MB, an extravascular 1 MB, a cardiac pacemaker implanted outside of the heart 104 but coupled to intracardiac or epicardial leads, or an intracardiac pacing device. One or more such devices may generate signals, and include processing circuitry configured to perform, in whole or in part, the techniques described herein.

In some examples, IMD 106 may be connected to leads that extend into (or on) heart 104 or could be implanted in heart 104 entirely. In the illustrated example, IMD 106 is coupled to a ventricular lead 112 and an atrial lead 114. Ventricular lead 112 and atrial lead 114 may be electrically coupled to IMD 106 and extend into (or on) the patient's heart 104. Ventricular lead 112 may include electrodes 116 and 118 shown positioned on the lead in or on the patient's right ventricle (RV) for sensing EGM signals and pacing in the RV. Atrial lead 114 may include electrodes 120 and 122 positioned on the lead in or on the patient's right atrium (RA) for sensing atrial EGM signals and pacing in the RA.

IMD 106 may use both ventricular lead 112 and atrial lead 114 to acquire cardiac electrogram (EGM) signals (e.g., to sense a cardiac signal that IMD 106 monitors for cardiac condition) from heart 104 of patient 102. Medical device system 100 is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 114.

In the example illustrated in FIG. 1, IMD 106 is coupled to ventricular lead 112 and atrial lead 114 that are fed through vasculature of patient 102. In some examples, IMD 106 may be configured to deliver cardiac therapy through leads that are configured to be implanted extravascularly coupled to electrodes that are configured to be implanted extravascularly. For instance, the lead(s) for cardiac therapy may be configured to be implanted percutaneously to couple to IMD 106 on a proximal end and be placed near the sternum on a distal end. The lead(s) for cardiac therapy may be coupled to electrodes that are proximate to heart 104 or on heart 104, but need not be implanted vascularly.

In accordance with one or more examples described in this disclosure, in addition to providing cardiac therapy and/or monitoring cardiac signals, IMD 106 is configured to deliver sleep apnea therapy. Sleep apnea may include Obstructive Sleep Apnea (OSA) and/or Central Sleep Apnea (CSA). IMD 106 may be configured to deliver stimulation to selected muscles and/or nerves for treatment of different mechanisms of sleep apnea, such as OSA, CSA, and/or a combination thereof. As discussed herein, a combination of OSA and CSA may also be referred to as multiple or comprehensive Sleep Apnea or generally as mixed sleep apnea (MSA). Stimulation of a lingual muscle (i.e. tongue) may assist in treatment of OSA, while stimulation of a Phrenic nerve (PN) or the diaphragm may assist in treating CSA. The stimulation may be provided to ensure maintaining an open airway and/or re-open an airway and/or cause movement of the diaphragm.

For instance, in the example illustrated in FIG. 1, IMD 106 is coupled to lead 124. Lead 124 may be percutaneously implanted and advanced to be implanted within a tongue of patient 102, as illustrated in more detail in FIG. 2. For instance, the electrodes located near the distal end of lead 124 may be configured to deliver electrical stimulation proximate motor points of one or both hypoglossal nerves of patient 102, which cause the tongue to advance forward, open the airway, and provide relief for OSA. As also illustrated in FIG. 1, IMD 106 is coupled to lead 126. The distal end of lead 126 may include one or more electrodes implanted near a phrenic nerve of patient 102, and IMD 106 may deliver electrical stimulation to the phrenic nerve, which may in turn cause contraction of the diaphragm. Accordingly, stimulating the phrenic nerve may cause movement or contraction of the diaphragm. For CSA, contraction of the diaphragm may be lacking, and therefore, by delivering electrical stimulation to the phrenic nerve, patient 102 may experience relief for CSA.

Stimulation of the hypoglossal nerve and phrenic nerve is provided as one example, and should not be considered limiting. In some examples, IMD 106 may be configured to deliver stimulation to an ansa cervicalis, a glossopharyngeal nerve, a tensor veli, levator veli, and/or digastric anterior of patient 102, in addition to or instead of stimulation to the lingual muscle (e.g., via the hypoglossal nerve) and/or phrenic nerve to treat the various ways in which patient 102 may experience sleep apnea. For example, by stimulating the ansa cervicalis, IMD 106 may provide therapy to address medial/lateral collapse. Accordingly, IMD 106 may be configured to deliver sleep apnea therapy that addresses the various mechanisms by which patient 102 may experience sleep apnea, and the delivery of sleep apnea therapy should not be considered limited to the above examples.

Figure 2:
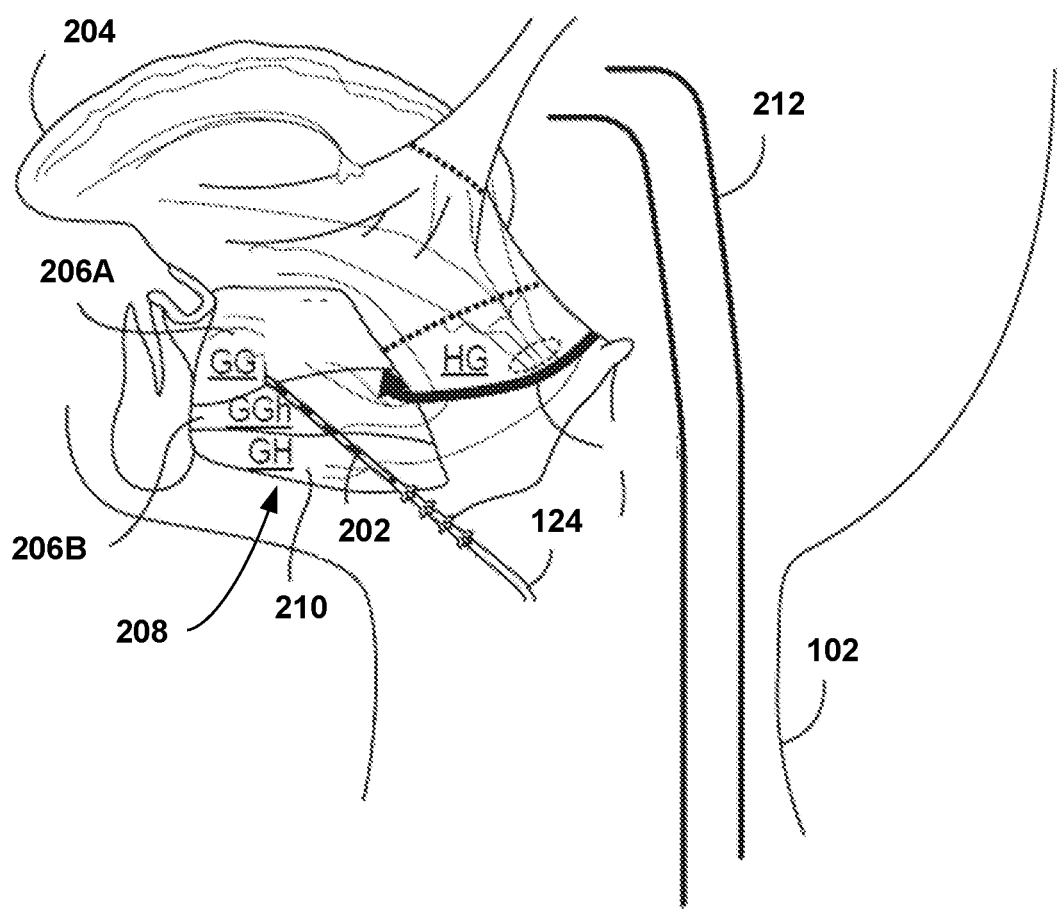
FIG. 2 is a conceptual diagram of an example IMD for delivering sleep apnea therapy according to one or more examples.

FIG. 2 is a conceptual diagram of an example for delivering sleep apnea therapy according to one or more examples. Lead 124 extends from IMD 106 of FIG. 1 to support delivery of sleep apnea therapy. Although one lead 124 is illustrated in FIGS. 1 and 2, there may be one or more leads 124 to which IMD 106 is coupled.

Lead 124 may include a flexible, elongate lead body, also called elongated member, that extends from a lead proximal end (e.g., end that couples to IMD 106) to a lead distal end (e.g., end that includes electrodes 202). As illustrated, lead 124 includes one or more electrodes 202 that are carried along a distal end and are configured for insertion within the protrusor muscles 206A, 206B, and 208 of tongue 204. As one example, the genioglossus muscle includes oblique compartment 206A and horizontal compartment 206B. In this disclosure, the genioglossus muscle is referred to as protrusor muscle 206. Protrusor muscle 208 is an example of the geniohyoid muscle.

As illustrated, the distal end of lead 124 includes one or more electrodes 202. The proximal end of lead 124 includes one or more electrical contacts to connect to a connector assembly that couples to IMD 106. Lead 124 also includes conductors such as coils or wires that connect respective electrodes 202 to respective electrical contacts at the proximal end of lead 124.

While protrusor muscles 206 and 208 are described, the example techniques described in this disclosure are not limited to stimulating protrusor muscles 206 and 208. Also, FIG. 2 illustrates one set of protrusor muscles 206 and 208 (e.g., on a first side of tongue 204). The other side of tongue 204 also includes protrusor muscles. For instance, a left side of tongue 204 includes a first set of protrusor muscles 206 and 208, and a right side of tongue 204 includes a second set of protrusor muscles.

In some examples, a surgeon may implant one or more leads 124 such that one or more electrodes 202 are implanted within soft tissue, such as musculature, proximate to medial branches of one or both hypoglossal nerves. In some examples, one or more electrodes 202 may be approximately 5 mm (e.g., 2 mm to 8 mm) from a major trunk of the hypoglossal nerve. In some examples, one or more electrodes 202 may be placed in an area of protrusor muscles 206 and 208 that include motor points, where each nerve axon terminates in the muscle (also called the neuro-muscular junction). The motor points are not at one location but spread out in the protrusor muscles. Lead 124 may be implanted such that one or more electrodes 202 may be generally in the area of the motor points (e.g., such that the motor points are within 1 to 10 mm from one or more electrodes 202). Accordingly, in some examples, electrodes 202 may be proximate to a hypoglossal nerve, but may not attach, connect, and/or touch a hypoglossal nerve.

Tongue 204 includes a distal end (e.g., tip of tongue 204), and electrodes 202 may be implanted proximate to root 210 of tongue 204. The surgeon may implant one or more leads 124 such that one or more electrodes 202 are implanted proximate to root 210 of tongue 204, as illustrated in FIG. 2. For example, the location for stimulation for the genioglossus muscle 206 may be approximately 30 mm (e.g., 25 mm to 35 mm) from the symphsis of the jaw (e.g., where the genioglossus and hypoglossal muscles insert). The location for stimulation for the geniohyoid muscle 208 may be approximately 40 mm (e.g., 35 mm to 45 mm) from the symphsis. For both the genioglossus muscle 206 and the geniohyoid muscle 208, the location for stimulation may be approximately 11 mm (e.g., 7 mm to 15 mm) lateral to the midline on both the right and left sides of tongue 204 for stimulating respective hypoglossal nerves.

In some examples, rather than or in addition to stimulating hypoglossal nerves, the examples described in this disclosure may be configured for stimulating the motor points. Stimulating the motor points may result in indirect activation of the hypoglossal nerve, but may generally be stimulating at a different location than direct stimulation to the hypoglossal nerve. As a result, in some examples, simulation of one or more motor points may result in more precise activation of muscle fibers than may be possible with stimulation of the hypoglossal nerve itself.

One or more electrodes 202 of lead 124 may be ring electrodes, segmented electrodes, partial ring electrodes or any suitable electrode configuration. Ring electrodes extend 360 degrees around the circumference of the lead body of lead 124. Segmented and partial ring electrodes each extend along an arc less than 360 degrees (e.g., 90-120 degrees) around the outer circumference of the lead body of lead 124. In this manner, multiple segmented electrodes may be disposed around the perimeter of lead 124 at the same axial position of the lead. In some examples, segmented electrodes may be useful for targeting different fibers of the same or different nerves at respective circumferential positions with respect to the lead to generate different physiological effects (e.g., therapeutic effects), permitting stimulation to be oriented directionally. In some examples, lead 124 may be, at least in part, paddle-shaped (e.g., a "paddle" lead), and may include an array of electrodes arranged as contacts or pads on a common surface, which may or may not be substantially flat and planar.

As described above, in some examples, electrodes 202 are within musculature of tongue 204. Accordingly, one or more electrodes 202 may be "intramuscular electrodes." Intramuscular electrodes may be different than other electrodes that are placed on or along a nerve trunk or branch, such as a cuff electrode, used to directly stimulate the nerve trunk or branch. The example techniques described in this disclosure are not limited to intramuscular electrodes and may be extendable to electrodes placed closer to a nerve trunk or branch of the hypoglossal nerve(s). Also, in some examples, rather than one or more electrodes 202 being "intramuscular electrodes," one or more electrodes 202 may be implanted in connective tissue or other soft tissue proximate to the hypoglossal nerve.

In some examples, lead 124 may be configured for advancement through the soft tissue, which may include the protrusor muscle tissue, to anchor electrodes 202 in proximity to the hypoglossal nerve(s) that innervated protrusor muscles 206 and/or 208 and/or motor points that connect axons of hypoglossal nerve(s) to respective muscle fibers of protrusor muscles 206 and/or 208. However, in some examples, lead 124 may be configured for advancement through vasculature of tongue 204. As one example, a surgeon may implant lead 124 in the lingual veins near the hypoglossal nerve though venous access in the subclavian vein. In such examples, one or more electrodes 202 may be "intravascular electrodes."

As described above, electrical stimulation therapy generated by IMD 106 and delivered via one or more electrodes 202 may activate protrusor muscles 206 and 208 to move tongue 204 forward, for instance, to promote a reduction in obstruction or narrowing of the upper airway 212 during sleep. As used herein, the term "activated" with regard to the electrical stimulation of protrusor muscles 206 and 208 refers to electrical stimulation that causes depolarization or an action potential of the cells of the nerve (e.g., hypoglossal nerve(s)) or stimulation at the neuro-muscular junction between the nerve and the protrusor muscles (e.g., at the motor points) innervating protrusor muscles 206 and 208 and motor points and subsequent depolarization and mechanical contraction of the protrusor muscle cells of protrusor muscles 206 and 208. In some examples, protrusor muscles 206 and 208 may be activated directly by the electrical stimulation therapy.

Protrusor muscles 206 and/or 208, on a first side of tongue 204 (e.g., the left or right side of tongue 204), may be activated by a medial branch of a first hypoglossal nerve, and the protrusor muscles, on a second side of tongue 204 (e.g., the other of the left or right side of tongue 40), may be activated by a medial branch of a second hypoglossal nerve. The medial branch of a hypoglossal nerve may also be referred to as the XIIth cranial nerve. The hyoglossus and styloglossus muscles (not shown in FIG. 1), which cause retraction and elevation of tongue 204, are activated by a lateral branch of the hypoglossal nerve.

One or more electrodes 202 may be used to deliver bilateral or unilateral stimulation to protrusor muscles 206 and 208 via the medial branch of the hypoglossal nerve or branches of the hypoglossal nerve (e.g., such as at the motor point where a terminal branch of the hypoglossal nerve interfaces with respective muscle fibers of protrusor muscles 206 and/or 208). For example, one or more electrodes 202 may be coupled to output circuitry (e.g., therapy delivery circuitry) of IMD 106 to enable delivery of electrical stimulation pulses in a manner that selectively activates the right and left protrusor muscles (e.g., in a periodic, cyclical or alternating pattern) to avoid muscle fatigue while maintaining upper airway patency. Additionally, or alternatively, IMD 106 may deliver electrical stimulation to selectively activate protrusor muscles 206 and/or 208 or portions of protrusor muscles 206 and/or 208 during unilateral stimulation of the left or right protrusor muscles.

In some examples, one lead 124 may be implanted such that one or more of electrodes 202 deliver electrical stimulation to stimulate the left hypoglossal nerve or motor points of protrusor muscles on the left side of tongue, and therefore cause the left protrusor muscles to activate. In such examples, the electrical stimulation from one or more electrodes 202 may not be of sufficient amplitude to stimulate the right hypoglossal nerve or motor points of protrusor muscles on the right side of tongue and cause the right protrusor muscles to activate. In some examples, one lead 124 may be implanted such that one or more of electrodes 202 deliver electrical stimulation to stimulate the right hypoglossal nerve or motor points of protrusor muscles on the right side of tongue, and therefore cause the right protrusor muscles to activate. In such examples, the electrical stimulation from one or more electrodes 202 may not be of sufficient amplitude to stimulate the left hypoglossal nerve or motor points of protrusor muscles on the left side of tongue and cause the left protrusor muscles to activate. Accordingly, in some examples, two leads like lead 124 may be implanted to stimulate each of the left and right hypoglossal nerves and/or motor points of respective protrusor muscles on the left and right side of tongue 204.

In some examples, one lead 124 may be implanted substantially in the middle (e.g., center) of tongue 204. In such examples, one or more electrodes 202 may deliver electrical stimulation to both hypoglossal nerves or motor points of both muscles on both sides of tongue 204, causing both hypoglossal nerves or motor points to activate respective left and right protrusor muscles. It may be possible to utilize current steering and field shaping techniques such that one or more electrodes 202 deliver first electrical stimulation that stimulates the left hypoglossal nerve or motor points of protrusor muscles on the left side of tongue 204 with little to no stimulation of the right hypoglossal nerve or motor points of protrusor muscles on the right side of tongue 204, and then one or more electrodes 202 deliver second electrical stimulation that stimulates the right hypoglossal nerve or motor points of protrusor muscles on the right side of tongue with little to no stimulation of the left hypoglossal nerve or motor points of protrusor muscles on the left side of tongue. In examples where two leads like lead 124 are utilized, each lead may alternate delivery of stimulation to respective hypoglossal nerves or motor points. In this way, IMD 106 may stimulate one hypoglossal nerve or one set of motor points and then the other hypoglossal nerve or another set of motor points, which can reduce muscle fatigue.

For instance, continuous stimulation may cause protrusor muscles to be continuously in a protruded state. This continuous contraction may cause protrusor muscles 206 and/or 208 to fatigue. In such cases, due to fatigue, the stimulation may not cause protrusor muscles 206 and/or 208 to maintain a protruded state (or higher intensity of the electrical stimulation may be needed to cause protrusor muscles 206 and/or 208 to remain in the protruded state). By stimulating one set of protrusor muscles (e.g., left or right), a second set (e.g., other of left or right) of protrusor muscles can be at rest. Stimulation may then alternate to stimulate the protrusor muscles that were at rest and thereby maintain protrusion of tongue 204, while permitting the protrusor muscles 206 and/or 208 that were previously activated to rest. Hence, by cycling between alternate stimulation of the left and right protrusor muscles, tongue 204 can remain in the protruded state, while one of the first or second set of protrusor muscles is at rest.

In some examples, one lead 124 may be implanted laterally or diagonally across tongue 204 such that some of electrodes 202 on lead 124 can be used to stimulate the left hypoglossal nerve and/or motor points of the protrusor muscles on the left side of tongue 204 and some of electrodes 202 on the same lead 124 can be used to stimulate the right hypoglossal nerve and/or motor points of the protrusor muscles on the right side of tongue 204. In such examples, IMD 106 may selectively deliver electrical stimulation to a first hypoglossal nerve and/or first motor points of the protrusor muscles on a first side of tongue 204 via a first set of one or more electrodes 202, and then deliver electrical stimulation to a second hypoglossal nerve and/or/or second set of motor points of the protrusor muscles on a second side of tongue 204 via a second set of one or more electrodes 202. This may be another way in which to reduce muscle fatigue.

There may be various ways in which lead 124 is implanted in patient 102. As one example, a surgeon may insert a needle (also called introducer needle) through the lower part of the jaw and in tongue 204 starting from the back of tongue 204. The surgeon may insert the needle until a distal tip of the needle reaches a point at or adjacent to musculature of protrusor muscles 206 and 208, angling the needle to be extended proximate to the hypoglossal nerve (e.g., left or right hypoglossal nerve) and to the motor points. In some examples, the needle may include one or more electrodes (e.g., one to four electrodes) at the distal end, and the surgeon may cause the one or more electrodes of the needle to output electrical stimulation (e.g., in the form of controlled current pulses or controlled voltage pulses), which in turn causes a physiological response such as activation of protrusor muscles 206 and/or 208 and advancing of tongue 204. The surgeon may adjust the location of the needle based on the physiological response to determine a location in tongue 204 that provides effective treatment. Using a needle with stimulating electrodes is not necessary in every example.

Once the needle is in place, the surgeon may insert a guidewire (or simply "guide") through the needle and anchor the guidewire (e.g., with tines on the guidewire) to tissue of tongue 204. Then, the surgeon may remove the needle, leaving behind the guidewire.

The surgeon may place an introducer, which may or may not include a dilator, over the guidewire through the opening created by the needle. The introducer may be referred to as an introducer, introducer sheath, or introducer/dilator. In some examples, the introducer may optionally include one or more electrodes that the surgeon can use to test stimulation of tongue 204 to ensure that lead 124 will be located in the correct location, relative to the target nerve tissue (e.g., motor points). Once the introducer is in place, the surgeon may remove the guidewire. In some examples, the introducer may be flexible or curved to ease placement of the introducer in patient 102.

The surgeon may prepare lead 124 for insertion. In some examples, there may be an additional sheath placed over lead 124 that holds fixation member(s) in place. Use of such an additional sheath is not necessary in all examples. Because lead 124 may be highly flexible, in some examples, the surgeon may place a stylet through lead 124 to provide some rigidity and allow lead 124 to traverse through tongue 204 under a pushing force. Use of a stylet may not be necessary in all examples.

The surgeon may put lead 124 through the introducer such that one or more electrodes 202 are proximate to the hypoglossal nerve. Electrodes 202 may be proximate to the hypoglossal nerve and/or motor points of the protrusor muscles due to the needle creating an opening near the hypoglossal nerve and/or motor points of the protrusor muscle. The surgeon may then tunnel the proximal end of lead 124 back to a connection with IMD 106.

In this manner, the surgeon may implant one lead 124. In examples where two or more leads are implanted, the surgeon may perform steps similar to those described above.

The above describes some example techniques for lead placement, and the examples described in this disclosure should not be considered limited to such examples of lead placement. Moreover, in some examples, the surgeon may use imaging techniques, such as fluoroscopy, during implantation to verify proper placement of lead 124, the needle, and/or the introducer.

Figure 3:
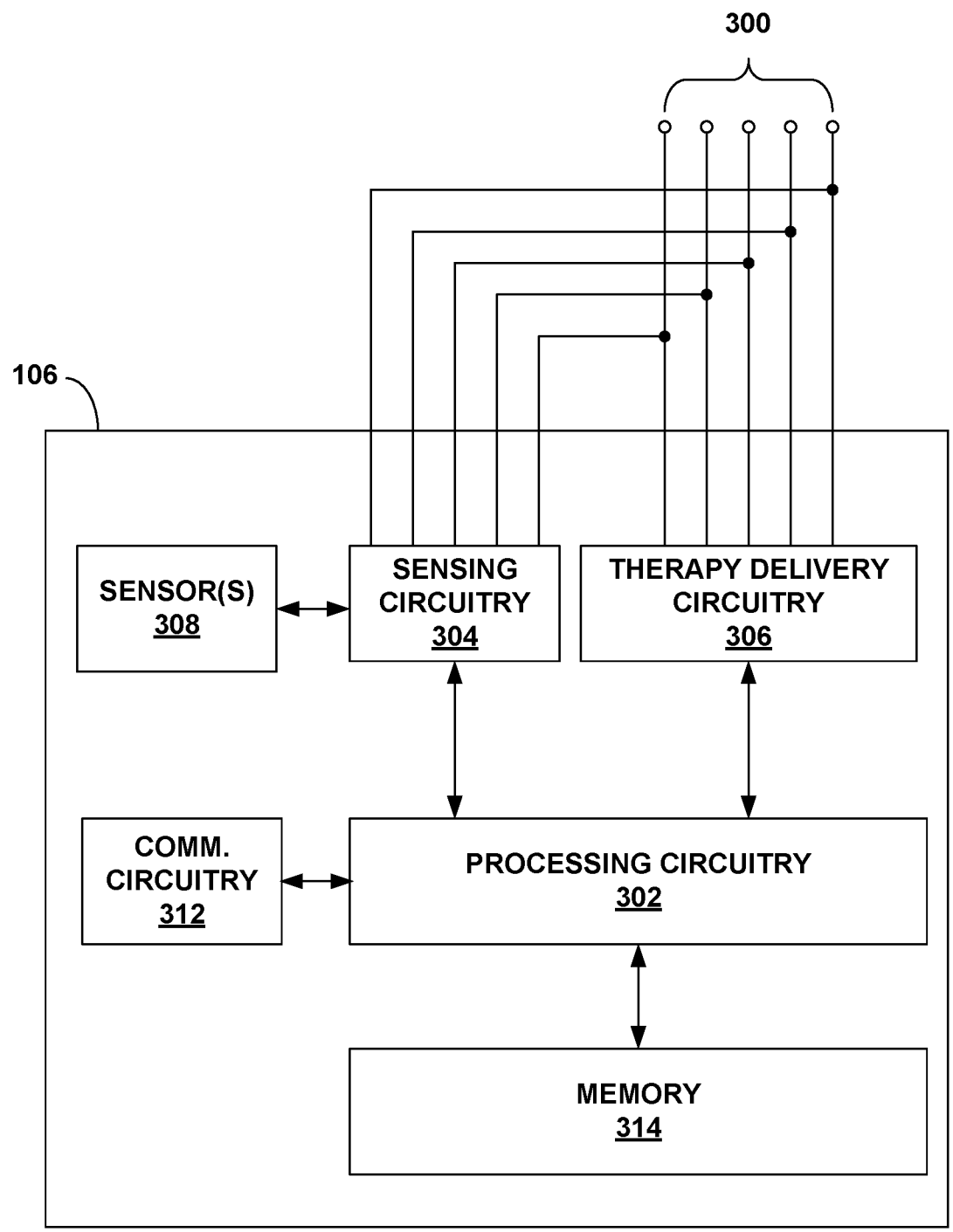
FIG. 3 is block diagram illustrating example configuration of an IMD which may be utilized in the system of FIG. 1.

FIG. 3 is block diagram illustrating example configuration of an IMD which may be utilized in the system of FIG. 1. As illustrated, IMD 106 includes processing circuitry 302, sensing circuitry 304, therapy delivery circuitry 306, one or more sensors 308, communication circuitry 312, and memory 314. FIG. 3 is a functional block diagram illustrating an example configuration of a medical device 106. However, medical device 106 does not need to include all these components in some examples, or medical device 106 may include additional components in some examples.

Therapy delivery circuitry 306 is illustrated as being coupled to electrodes 300. Electrodes 300 are examples of electrodes 202, 116, 118, 120, and 122, and electrodes coupled to lead 126 for stimulating the phrenic nerve. That is, a first set of electrodes 300 may be configured to be implanted for delivery of sleep apnea therapy (e.g., such as electrodes 202, electrodes at the end of lead 126, or electrodes located near ansa cervicalis, a glossopharyngeal nerve, a tensor veli, levator veli, and/or digastric anterior of patient 102), and a second set of electrodes 300 may be configured to be implanted for delivery of cardiac therapy. For ease of illustration, electrodes 300 are shown to collectively represent the electrodes used for sleep apnea therapy and cardiac therapy.

Although one therapy delivery circuitry 306 is illustrated as delivering electrical stimulation to electrodes 300, the example techniques are not so limited. In some examples, a portion of therapy delivery circuitry 306 may be specifically configured to deliver sleep apnea therapy, and another portion of therapy delivery circuitry 306 may be specifically configured to deliver cardiac therapy. For example, therapy delivery circuitry 306 may be common circuitry to deliver the cardiac therapy and the sleep apnea therapy. As another example, therapy delivery circuitry 306 may include cardiac therapy delivery circuitry configured to deliver the cardiac therapy, and sleep apnea therapy delivery circuitry configured to deliver the sleep apnea therapy.

In some examples, the range of the cardiac therapy parameters and the sleep apnea therapy parameters may be substantially different. Examples of the cardiac therapy parameters and the sleep apnea therapy parameters include amplitude, frequency, pulse width, duration, waveform, etc. For cardiac therapy, the range of amplitude, frequency, pulse width, duration, waveform etc. that provides effective therapy may be different than the range of amplitude, frequency, pulse width, duration, waveform etc. for sleep apnea therapy. Therefore, in some examples, therapy delivery circuitry 306 may include different circuitry configured specifically for delivering sleep apnea therapy (e.g., sleep apnea therapy delivery circuitry) or cardiac therapy (e.g., cardiac therapy delivery circuitry). Having specialized circuitry for sleep apnea therapy or cardiac therapy is provided as one example, and should not be considered limiting.

In one or more examples, therapy delivery circuitry 306 may be configured to deliver sleep apnea therapy and cardiac therapy simultaneously or at different times. For instance, the sleep apnea therapy and the cardiac therapy may be separate in time or partially or fully overlapping in time. For some therapies, like cardiac pacing therapy, therapy delivery circuitry 306 may deliver such therapy on a persistent or continuous basis, while for other therapies, like sleep apnea or cardiac defibrillation therapy, therapy delivery circuitry 306 may deliver such therapy on an on-demand or as-needed basis.

Therapy delivery circuitry 306 is described as delivering both sleep apnea therapy and cardiac therapy. However, in some examples, therapy delivery circuitry 306 may deliver sleep apnea therapy but may not deliver cardiac therapy. In such examples, IMD 106 via sensing circuitry 304 may sense a cardiac signal but there may not be delivery of therapy. Processing circuitry 302 may monitor the cardiac signal sensed with sensing circuitry 304 (e.g., such as to detect a cardiac condition). In some examples, sensing circuitry 304 may sense a cardiac signal that processing circuitry 302 monitors, and in addition therapy delivery circuitry 306 may be configured to deliver cardiac therapy and sleep apnea therapy.

Memory 314 may include computer-readable instructions that, when executed by processing circuitry, cause medical device 106 and processing circuitry 302 to perform various functions attributed to medical device 106 and processing circuitry 302 herein. Memory 314 may include any volatile, non-volatile, magnetic, optical, or electrical media, such as a random access memory (RAM), read-only memory (ROM), non-volatile RAM (NVRAM), ferroelectric RAM (FRAM), electrically-erasable programmable ROM (EEPROM), flash memory, or any other digital or analog media.

Processing circuitry 302 may include fixed function circuitry and/or programmable processing circuitry. Processing circuitry 302 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 302 may include multiple components, such as any combination of one or more microprocessors, one or more controllers, one or more DSPs, one or more ASICs, or one or more FPGAs, as well as other discrete or integrated logic circuitry. The functions attributed to processing circuitry 302 herein may be embodied as software, firmware, hardware or any combination thereof.

Sensing circuitry 304 and therapy delivery circuitry 306 are coupled to electrodes 300. Sensing circuitry 304 may sense signals from a selected two or more of electrodes 300 in order for processing circuitry 302 to monitor electrical activity of heart, impedance, or other electrical phenomenon, sensing tone of muscles 206 and/or 208 (e.g., based on electromyography (EMG) signal), etc. Sensing of a cardiac signal may be done to determine heart rates or HRV (heart rate variability), or to detect arrhythmias (e.g., tachyarrhythmias or bradycardia) or other electrical signals. For example, processing circuitry 302 may monitor the cardiac signal sensed with sensing circuitry 304 to determine HRV or detect arrhythmias such as atrial tachyarrhythmias and ventricular arrythmias, or more generally detect a cardiac condition including heart failure, possibility of sudden death or epilepsy. In some examples, sensing circuitry 304 may include one or more filters and amplifiers for filtering and amplifying a signal received from electrodes 300. In some examples, sensing circuitry 304 may sense or detect physiological parameters, such as heart rate, blood pressure, respiration, and the like. Heart rate and blood pressure are additional examples of a cardiac signal that sensing circuitry 304 may sense.

In some examples, there may be benefits in sensing cardiac signals and monitoring cardiac signals. For example, sleep apnea is correlated with AF (atrial fibrillation), HF (heart failure), HTN (hypertension), etc. The ability to sense and monitor cardiac signals may be useful managing AF, HF, HTN etc., regardless of whether IMD 106 can provide cardiac therapy. For instance, sensing circuitry 304 and processing circuitry 302 may monitor cardiac signals that include tachyarrythmias (VT/VF and AF) and bradyarrhythmias. In some examples, sensing circuitry through sensor(s) 308 and processing circuitry 302 may sense and monitor respiration (key metric for many other disease states like COPD, Diabetes, HF, etc.), HF (fluid status like OptiVol).

The resulting cardiac electrical signal may be passed to processing circuitry 302 configured to monitor a cardiac signal sensed by the sensing circuitry 304. For example, to monitor the cardiac signal, processing circuitry 302 may detect a cardiac event when the cardiac electrical signal crosses a sensing threshold. The cardiac event detection circuitry may include a rectifier, filter and/or amplifier, a sense amplifier, comparator, and/or analog-to-digital converter. In general, processing circuitry 302 may monitor the cardiac signal to generation information indicative of a cardiac condition.

Sensing circuitry 304, in some examples, may also be configured to sense electrical signals generated within tongue 204. For example, sensing circuitry 304 may sense an EMG signal within tongue 204, and determine a muscle tone of tongue 204. If the EMG signal indicates that tongue 204 is relaxed, there may be a chance that patient 102 is going to experience sleep apnea, but if the EMG signal indicates that tongue 204 is activated, there may be a reduced chance that patient 102 is going to experience sleep apnea.

In some examples, sensing circuitry 304 may sense EEG (electroencephalogram). Processing circuitry 302 (or possibly other processing circuitry) may determine effectiveness of sleep apnea therapy based on the EEG. For instance, the quality of sleep may be derived from the EEG, and high quality of sleep may be indicative of low apneic episodes. Sensing circuitry 304 may be coupled to the electrodes placed more proximate to the brain for sending EEG. In some examples, the electrodes 202 may be sufficiently close to the brain for sensing EEG.

Sensing circuitry 304 may also include a switch module to select which of the available electrodes 300 (or electrode polarities) are used to sense the heart or tongue activity. In examples with several electrodes 300, processing circuitry 302 may select the electrodes that function as sense electrodes, i.e., select the sensing configuration, via the switch module within sensing circuitry 304.

In the example of FIG. 3, medical device 106 includes one or more sensors 308 coupled to sensing circuitry 304. Although illustrated in FIG. 3 as being included within medical device 106, one or more of sensors 308 may be external to medical device 106, e.g., coupled to medical device 106 via one or more leads, or configured to wirelessly communicate with medical device 106. In some examples, sensors 308 transduce a signal indicative of a patient parameter, which may be amplified, filtered, or otherwise processed by sensing circuitry 304. In such examples, processing circuitry 302 determines physiological parameter value (s) based on the signals. In some examples, sensors 308 determine the physiological parameter value(s), and communicate them, e.g., via a wired or wireless connection, to processing circuitry.

In some examples, sensors 308 include one or more accelerometers, e.g., one or more three-axis accelerometers. Signals generated by the one or more accelerometers may be indicative of, for example, heart sounds or other vibrations or movement associated with the beating of the heart, or coughing, rales, or other respiration abnormalities. The signals from the accelerometers may also indicate whether patient 102 is lying down or upright, which may indicate if patient 102 is sleeping or not. The accelerometers may produce and transmit signals to processing circuitry 302 for a determination as to whether the heart 104 has contracted, whether patient 102 is sleeping, etc. In some examples, sensors 308 may include one or more microphones configured to detect heart sounds or respiration abnormalities, such as snoring which may indicate sleep apnea. In some examples, sensors 308 may include sensors configured to transduce signals indicative of blood flow, oxygen saturation of blood, or patient temperature, and processing circuitry 302 may determine patient parameters values based on these signals.

In some examples, therapy delivery circuitry 306 is configured to generate and deliver sleep apnea therapy or both cardiac therapy and sleep apnea therapy. Therapy delivery circuitry 306 may include one or more pulse generators, capacitors, and/or other components capable of generating and/or storing energy to deliver as pacing therapy, defibrillation therapy, cardioversion therapy, other therapy or a combination of therapies. Therapy delivery circuitry 306 may also include circuitry to deliver stimulation signal to stimulate the motor points near the hypoglossal nerve, the hypoglossal nerve, the phrenic nerve, and other nerves for treating sleep apnea such as OSA and CSA. In some instances, therapy delivery circuitry 306 may include a first set of components configured to provide pacing therapy, a second set of components configured to provide anti-tachyarrhythmia shock therapy, a third set of components configured to provide OSA therapy, and a fourth set of components configured to provide CSA therapy. In other instances, therapy delivery circuitry 306 may utilize the same set of components to provide both pacing and anti-tachyarrhythmia shock therapy, and OSA and CSA therapy. In still other instances, therapy delivery circuitry 306 may share some of the pacing and shock therapy components while using other components solely for pacing or shock delivery, and similarly share some of the components for both cardiac and sleep apnea therapy while using other components solely for cardiac or sleep apnea therapy.

Therapy delivery circuitry 306 may include charging circuitry, one or more charge storage devices, such as one or more capacitors, and switching circuitry that controls when the capacitor(s) are discharged to electrodes 300 and the widths of pulses. Charging of capacitors to a programmed pulse amplitude and discharging of the capacitors for a programmed pulse width may be performed by therapy delivery circuitry 306 according to control signals received from processing circuitry, which are provided by processing circuitry according to parameters stored in memory 314. Processing circuitry may control therapy delivery circuitry 306 to deliver the generated therapy to the heart via one or more combinations of electrodes 300, e.g., according to parameters stored in memory 314. Therapy delivery circuitry 306 may include switch circuitry to select which of the available electrodes 300 are used to deliver the therapy, e.g., as controlled by processing circuitry.

For sleep apnea therapy, therapy delivery circuitry 306 may be configured to deliver sleep apnea therapy, examples of which include includes one or more of obstructive sleep apnea (OSA) therapy, central sleep apnea (CSA) therapy, and mixed apnea therapy (e.g., treating OSA and CSA simultaneously). Examples of the OSA therapy include anterior/posterior collapse therapy, and medial/lateral collapse therapy. Therapy delivery circuitry 306 may include independent current or voltage sources coupled to respective ones of electrodes 300 used for sleep apnea therapy. For instance, processing circuitry 302 may configure electrodes 202 on lead 124 as anode or cathode electrodes and deliver stimulation using the electrodes designated as anodes and cathodes. In general, therapy delivery circuitry 306 may include various types of components that can be used for delivering cardiac therapy and sleep apnea therapy.

As one example, the sleep apnea therapy parameters may include:
a. Frequency or pulse rate: between about 30 Hz and about 50 Hz. In some examples, the minimum target frequency is used which can achieve muscle tetany (e.g., constant contraction) and provide the required force to open the airway.
b. Current Amplitude: between about 0.5 milliamps (mA) and about 10 mA, and more generally from 0.5 mA to 3 mA, and approximately 1.5 mA.
c. Pulse Width: between about 100 microseconds (µs) and about 500 µs.
In some examples, a pulse width of 150 µs might be used for reduced power consumption. In some particular examples, the pulse width is approximately 210 µs.
In some cases, shorter pulse widths may be used in conjunction with higher current or voltage amplitudes.

As described, therapy delivery circuitry 306 may be configured to also deliver cardiac therapy. In some examples, processing circuitry 302 may determine that cardiac therapy is to be delivered based on electrical signals sensed by sensing circuitry 304. For instance, processing circuitry 302 may include a timing and control module, which may be embodied as hardware, firmware, software, or any combination thereof. The timing and control module may comprise a dedicated hardware circuit, such as an ASIC, separate from other processing circuitry 302 components, such as a microprocessor, or a software module executed by a component of processing circuitry 302, which may be a microprocessor or ASIC. The timing and control module may implement programmable counters, and such counters may control the basic time intervals associated with DDD, VVI, DVI, VDD, AAI, DDI, DDDR, VVIR, DVIR, VDDR, AAIR, DDIR and other modes of pacing. In the example modes of pacing, the first letter defines the pacing chamber(s): ventricle (V), atrium (A), both (D), or none (O). The second letter defines the sensing chamber(s): ventricle (V), atrium (A), both (D), or none (O). The third letter defines the mode of operation: inhibited (I), triggered (T), dual (D, I+T), or none (O). The fourth letter indicates whether there is rate modulation (rate response, R).

Intervals defined by the timing and control module within processing circuitry 302 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing circuitry 304 for a time interval during and after delivery of electrical stimulation to heart 104. The durations of these intervals may be determined by processing circuitry 302 in response to stored data in memory 314. The timing and control module of processing circuitry 302 may also determine the amplitude of the cardiac pacing pulses.

Interval counters implemented by the timing and control module of processing circuitry 302 may be reset upon sensing of R-waves and P-waves with detection channels of sensing circuitry 304. The value of the count present in the interval counters when reset by sensed R-waves and P-waves may be used by processing circuitry 302 to measure the durations of R-R intervals, P-P intervals, P-R intervals and R-P intervals, which are measurements that may be stored in memory 314. Processing circuitry 302 may use the count in the interval counters to detect a tachyarrhythmia event, such as AF (atrial fibrillation), AT (atrial tachycardia), VF (ventricular fibrillation), or VT (ventricular tachycardia). These intervals may also be used to detect the overall heart rate, ventricular contraction rate, and heart rate variability. A portion of memory 314 may be configured as a plurality of recirculating buffers, capable of holding series of measured intervals, which may be analyzed by processing circuitry 302 in response to the occurrence of a pace or sense interrupt to determine whether the patient's heart 104 is presently exhibiting atrial or ventricular tachyarrhythmia. In some examples, an arrhythmia detection method may include any suitable tachyarrhythmia detection algorithms.

In some examples, processing circuitry 302 may determine that tachyarrhythmia has occurred by identification of shortened R-R (or P-P) interval lengths. Generally, processing circuitry 302 detects tachycardia when the interval length falls below 220 milliseconds and fibrillation when the interval length falls below 180 milliseconds. In other examples, processing circuitry 302 may detect ventricular tachycardia when the interval length falls between 330 milliseconds and ventricular fibrillation when the interval length falls between 240 milliseconds. These interval lengths are merely examples, and a user may define the interval lengths as desired, which may then be stored within memory 314. This interval length may need to be detected for a certain number of consecutive cycles, for a certain percentage of cycles within a running window, or a running average for a certain number of cardiac cycles, as examples.

In the above examples, processing circuitry 302 is described as detecting or determining a cardiac condition (e.g., various types of arrhythmias) by monitoring the cardiac signal sensed by sensing circuitry 304. Processing circuitry 302 may then cause therapy delivery circuitry 306 to deliver cardiac therapy. However, in some examples, therapy delivery circuitry 306 may not deliver cardiac therapy, but processing circuitry 302 may still monitor the cardiac signal.

For delivery of cardiac therapy, processing circuitry 302 controls therapy delivery circuitry 306 to deliver stimulation therapy to heart 104 according to therapy parameters, which may be stored in memory 314. For example, processing circuitry 302 may control therapy generating circuitry 306 to deliver electrical pulses with the amplitudes, pulse widths, frequency, or electrode polarities specified by the therapy parameters. In this manner, therapy delivery circuitry 306 may deliver pacing pulses (e.g., anti-tachyarrhythmia pacing (ATP) pulses or post-shock pacing therapy, or conventional bradycardia pacing pulses) to heart 104 via electrodes 116, 118, 120, and/or 122. IMD 106 may use any combination of electrodes to deliver therapy and/or detect electrical signals from patient 102. In general, processing circuitry 302 may control therapy delivery circuitry 306 to delivery cardiac therapy, examples of which include one or more of defibrillation therapy, cardiac resynchronization therapy (CRT), bradycardia therapy, and arrhythmia therapy.

Therapy delivery circuitry 306 may deliver pacing stimulation, e.g., ATP therapy or post-shock pacing, in the form of voltage or current electrical pulses. In other examples, therapy delivery circuitry 306 may deliver one or more of these types of stimulation in the form of other signals, such as sine waves, square waves, or other substantially continuous time signals. Although the above examples are generally described as delivering pacing pulses, IMD 106 may deliver cardioversion or defibrillation pulses in other examples. Furthermore, IMD 106 may deliver sleep apnea therapy as well.

ATP may be delivered to patient 102 as defined by a set of parameters, which may be stored in memory 314. These parameters may include pulse intervals, pulse width, current and/or voltage amplitudes, and durations for each pacing mode. For example, the pulse interval may be based on a fraction of the detected ventricular tachycardia (VT) cycle length and be between approximately 150 milliseconds and 500 milliseconds (e.g., between approximately 2.0 hertz and 7.0 hertz), and the pulse width may be between approximately 0.5 milliseconds and 2.0 milliseconds. The amplitude of each pacing pulse may be between approximately 2.0 volts and 10.0 volts. In some examples, the pulse amplitude may be approximately 6.0 V and the pulse width may be approximately 1.5 milliseconds; another example may include pulse amplitudes of approximately 5.0 V and pulse widths of approximately 1.0 milliseconds. Each train of pulses during ATP may last for a duration of between approximately 0.5 seconds to approximately 15 seconds or be defined as a specific number of pulses. Each pulse, or burst of pulses, may include a ramp up in amplitude or in pulse rate.

Parameters that define post-shock pacing may also vary. In one example, monophasic post-shock pacing therapy may have a pulse width of approximately 1 millisecond at each phase and a pulse amplitude of approximately 5 volts. The pacing rate may be set to 30-60 beats per minute (0.5-1 hertz). The duration of each post-shock pacing session may be between 10 seconds and 60 seconds, or even longer in other examples. In other examples, pulse widths, pulse amplitudes, and/or durations of post-shock pacing may be greater or lower.

In this way, IMD 106 is an example of a single IMD configured to deliver cardiac therapy and sleep apnea therapy in an integrated manner. For example, IMD 106 includes therapy delivery circuitry 306 and processing circuitry 302. Processing circuitry 302 may be configured to determine cardiac therapy parameters and sleep apnea therapy parameters. As one example, to determine the cardiac therapy parameters and the sleep apnea therapy parameters, processing circuitry 302 may receive the cardiac therapy parameters and the sleep apnea therapy parameters from memory 314. As another example, to determine the cardiac therapy parameters and the sleep apnea therapy parameters, processing circuitry 302 may receive the cardiac therapy parameters and the sleep apnea therapy parameters from external device 108. In some examples, IMD 106 may deliver sleep apnea therapy, but may not deliver cardiac therapy. IMD 106 may still be configured to monitor cardiac signals. In some examples, IMD 106 may be configured to deliver cardiac therapy, monitor cardiac signals, and deliver sleep apnea therapy.

As yet another example, processing circuitry 302 may be configured to determine the cardiac therapy parameters in response to sensing a condition associated with the sleep apnea therapy, or determine the sleep apnea therapy parameters in response to sensing a condition associated with the cardiac therapy. For example, when there is airway blockage, the chances of arrhythmia increase. Accordingly, in some examples, processing circuitry 302 may use the EMG signal sensed by sensing circuitry 304 to determine that tongue 204 has low tone, and may therefore block the airway. In response, processing circuitry 302 may change the sleep apnea therapy parameters, and may also change the cardiac therapy parameters to address any one or more issues from arrythmia.

As another example, processing circuitry 302 may determine that change in cardiac therapy parameters is needed based on cardiac signals sensed by sensing circuitry 304. For instance, there may be some stress on heart 104 that is causing changes in the polarization/depolarization of heart 104. In some cases, because sleep apnea can be a co-factor for a cardiac condition, processing circuitry 302 may change the sleep apnea therapy parameters to better ensure that tongue 204 remains advanced when patient 102 is sleeping to reduce the stress on heart 104.

As one example, changes in blood oxygen saturation while patient 102 is sleeping could be due to an apnea/hypopnea event (air not getting to the lungs) or a cardiac event resulting in poor circulation (e.g., a ventricular arrythmia). In some examples, IMD 106 (e.g., with sensing circuitry 304) may sense all three parameters—blood O2, apnea/hypopnea (AH) and cardiac rhythm/output. In such examples, processing circuitry 302 may detect and diagnose why the blood O2 levels are low. By tracking the correlation between O2 desaturation and AH and correlation between O2 desaturation and CO (cardiac output or arrythmia), processing circuitry 304 may prioritize or rule out the use of possible treatments like anti-tachypacing/defibrillation or raising the therapy amplitude for OSA or CSA. In some examples, processing circuitry 304 may determine that both cardiac and sleep apnea therapy are to be delivered simultaneously, such as in the example case described above.

As another example, a parameter that is affected by sleep apnea and directly effects cardiac function is the level of sympathetic drive. For instance, the sympathetic nervous system (SNS) releases hormones to accelerate the heart rate (HR). There may be changes to the sympathetic drive during an AH event. If there is release of hormones to accelerate heart rate, and high HR is detected, processing circuitry 302 may be configured to cause therapy delivery circuitry 306 to deliver vagal stimulation to slow heart rate and reduce contractility. In this way, having a unitary device for sleep apnea therapy and cardiac monitoring and/or cardiac therapy may provide therapeutic benefits.

Processing circuitry 302 may control therapy delivery circuitry 306 to deliver cardiac therapy via a first set of electrodes implantable within patient 102 in accordance with the cardiac therapy parameters and deliver sleep apnea therapy via a second set of electrodes implantable within patient 102 in accordance with the sleep apnea therapy parameters. Examples of the cardiac therapy parameters include those provided above for ATP and post-shock pacing, as some non-limiting examples, but other ranges of cardiac therapy parameters are possible. Examples of the sleep apnea therapy parameters include those provided above for the amplitude, pulse width, and frequency of the electrical stimulation signals delivered to the motor points of the hypoglossal nerve or to the hypoglossal nerve.

Examples of the first set of electrodes implantable within patient 102 for delivery of cardiac therapy include electrodes 116, 118, 120, and 122. However, there may be additional examples as well, such as examples of electrodes that are extravascularly implanted in a percutaneous manner, rather than being implanted vascularly. Examples of the second set of electrodes for delivery of sleep apnea therapy include electrodes 202, as well as electrodes at the end of lead 126 for delivering stimulation to the phrenic nerve. Additional examples of electrodes for delivering sleep apnea therapy include electrodes implanted in or near the ansa cervicalis, a glossopharyngeal nerve, a tensor veli, levator veli, and/or digastric anterior of patient 102.

Communication circuitry 312 may include any suitable hardware, firmware, software or any combination thereof for communicating with another device, such as an external device 108 or another IMD or sensor. Under the control of processing circuitry 302, communication circuitry 312 may receive downlink telemetry from and send uplink telemetry to an external device 108 or another device with the aid of an antenna, which may be internal and/or external. In some examples, communication circuitry 312 may communicate with a local external device, and processing circuitry 302 may communicate with a networked computing device via the local external device and a computer network, such as the Medtronic CareLink® Network. As described above, in some examples, CareLink® may be utilized to better manage therapy, as well as determine effectiveness of therapy. For instance, the physician may review CareLink® and determine whether a reduction or increase in the duration of sleep apnea therapy is needed to better control cardiac conditions.

A clinician or other user may retrieve data from medical device 106 using external device 108 or another local or networked computing device configured to communicate with processing circuitry via communication circuitry 312. The clinician may also program parameters of medical device 106 using external device 108 or another local or networked computing device. In some examples, communication with medical device 106 and external device 108 may be via RF telemetry.

Figure 4:
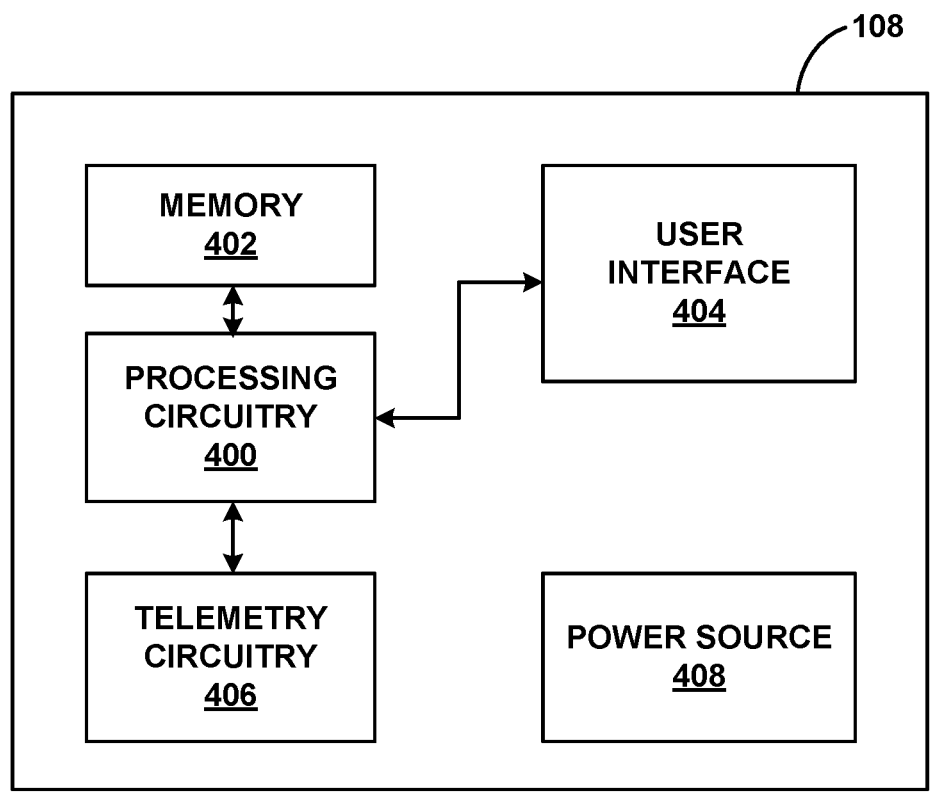
FIG. 4 is a block diagram illustrating an example configuration of an external device for use with an IMD according to one or more examples.

FIG. 4 is a block diagram illustrating an example configuration of an external device according to one or more examples. While programmer 108 may generally be described as a hand-held computing device, programmer 108 may be a notebook computer, a cell phone, or a workstation, for example. As illustrated in FIG. 4, external programmer 108 may include processing circuitry 400, memory 402, user interface 404, telemetry circuitry 406, and power source 408.

In general, programmer 108 comprises any suitable arrangement of hardware, alone or in combination with software and/or firmware, to perform the techniques attributed to programmer 108, and processing circuitry 400, user interface 404, and telemetry circuitry 406 of programmer 108. Examples of processing circuitry 400 may include one or more processors, such as one or more microprocessors, DSPs, ASICs, FPGAs, or any other equivalent integrated or discrete logic circuitry, as well as any combinations of such components. Examples of memory 402 include RAM, ROM, PROM, EPROM, EEPROM, flash memory, a hard disk, a CD-ROM, comprising executable instructions for causing the one or more processors to perform the actions attributed to them. Moreover, although processing circuitry 400 and telemetry circuitry 406 are described as separate circuitry, in some examples, processing circuitry 400 and telemetry circuitry 406 are functionally integrated. In some examples, processing circuitry 40 and telemetry circuitry 406 correspond to individual hardware units, such as ASICs, DSPs, FPGAs, or other hardware units.

In some examples, memory 402 may further include program information (e.g., stimulation programs) defining the electrical stimulation, similar to program information stored in memory 314 of IMD 106. The stimulation programs stored in memory 402 may be downloaded into memory 314 of IMD 106.

User interface 404 may include a button or keypad, lights, a speaker for voice commands, a display, such as a liquid crystal (LCD) or light-emitting diode (LED). In some examples the display may be a touch screen. As discussed in this disclosure, processing circuitry 400 may present and receive information relating to electrical stimulation and resulting therapeutic effects via user interface 404. For example, processing circuitry 400 may receive patient input via user interface 404. The input may be, for example, in the form of pressing a button on a keypad or selecting an icon from a touch screen.

Processing circuitry 400 may also present information to the patient in the form of alerts related to delivery of the electrical stimulation to patient 102 or a caregiver via user interface 404. Although not shown, programmer 108 may additionally or alternatively include a data or network interface to another computing device, to facilitate communication with the other device, and presentation of information relating to the electrical stimulation and therapeutic effects after termination of the electrical stimulation via the other device.

Telemetry circuitry 406 supports wireless communication between IMD 106 and programmer 108 under the control of processing circuitry 400. Telemetry circuitry 406 may also be configured to communicate with another computing device via wireless communication techniques, or direct communication through a wired connection. In some examples, telemetry circuitry 406 may be substantially similar to communication circuitry 312 of IMD 106 described above, providing wireless communication via an RF or proximal inductive medium. In some examples, telemetry circuitry 406 may include an antenna, which may take on a variety of forms, such as an internal or external antenna.

Examples of local wireless communication techniques that may be employed to facilitate communication between programmer 108 and another computing device include RF communication according to the 802.11 or Bluetooth specification sets, infrared communication (e.g., according to the IrDA standard), or other standard or proprietary telemetry protocols. In this manner, other external devices may be capable of communicating with programmer 108 without needing to establish a secure wireless connection.

Power source 408 delivers operating power to the components of programmer 108. Power source 408 may include a battery and a power generation circuit to produce the operating power. In some examples, the battery may be rechargeable to allow extended operation.

In accordance with one or more examples described in this disclosure, because programmer 108 may be configured to communicate with IMD 106, programmer 108 may be configured to provide options that allow a clinician or patient 102 to program both cardiac therapy parameters and sleep apnea therapy parameters so that processing circuitry 302 may determine cardiac therapy parameters and sleep apnea therapy parameters (e.g., receive them from programmer 108), and control therapy delivery circuitry 306 to deliver cardiac therapy via a first set of electrodes implantable within patient 102 in accordance with the cardiac therapy parameters and deliver sleep apnea therapy via a second set of electrodes implantable within patient 102 in accordance with the sleep apnea therapy parameters.

That is, with user interface 404, the clinician and/or patient 102, including caregiver, may enter cardiac therapy parameters and sleep apnea therapy parameters. Telemetry circuitry 406 may then output the cardiac therapy parameters and the sleep apnea therapy parameters to IMD 106. In some examples, user interface 404 may also display sensed signals, as sensed by sensing circuitry 304 or sensor(s) 308. For example, processing circuitry 302 may store information indicative of the sensed signals sensed by sensing circuitry 304 or sensor(s) 308 in memory 314. Processing circuitry 302 may then upload the information indicative of the sensed signals to programmer 108. User interface 404 may display the information indicative of the sensed signals, and the clinician may perform appropriate actions based on the sensed signals.

For example, the clinician may determine that changes in arrythmia coincide with reduction in tone of tongue 204 or increase in snoring (e.g., as determined by examples where one of sensors 308 is a microphone). In this example, user interface 404 may display the pattern of when there was change in arrythmia and changes in conditions related to sleep apnea. In such examples, to increase the efficacy of the therapy, rather than just changing the cardiac therapy parameters or just changing the sleep apnea therapy parameters, the clinician may change both the cardiac therapy parameters and the sleep apnea therapy parameters to better address the additional stress being placed on heart 104.

Figure 5:
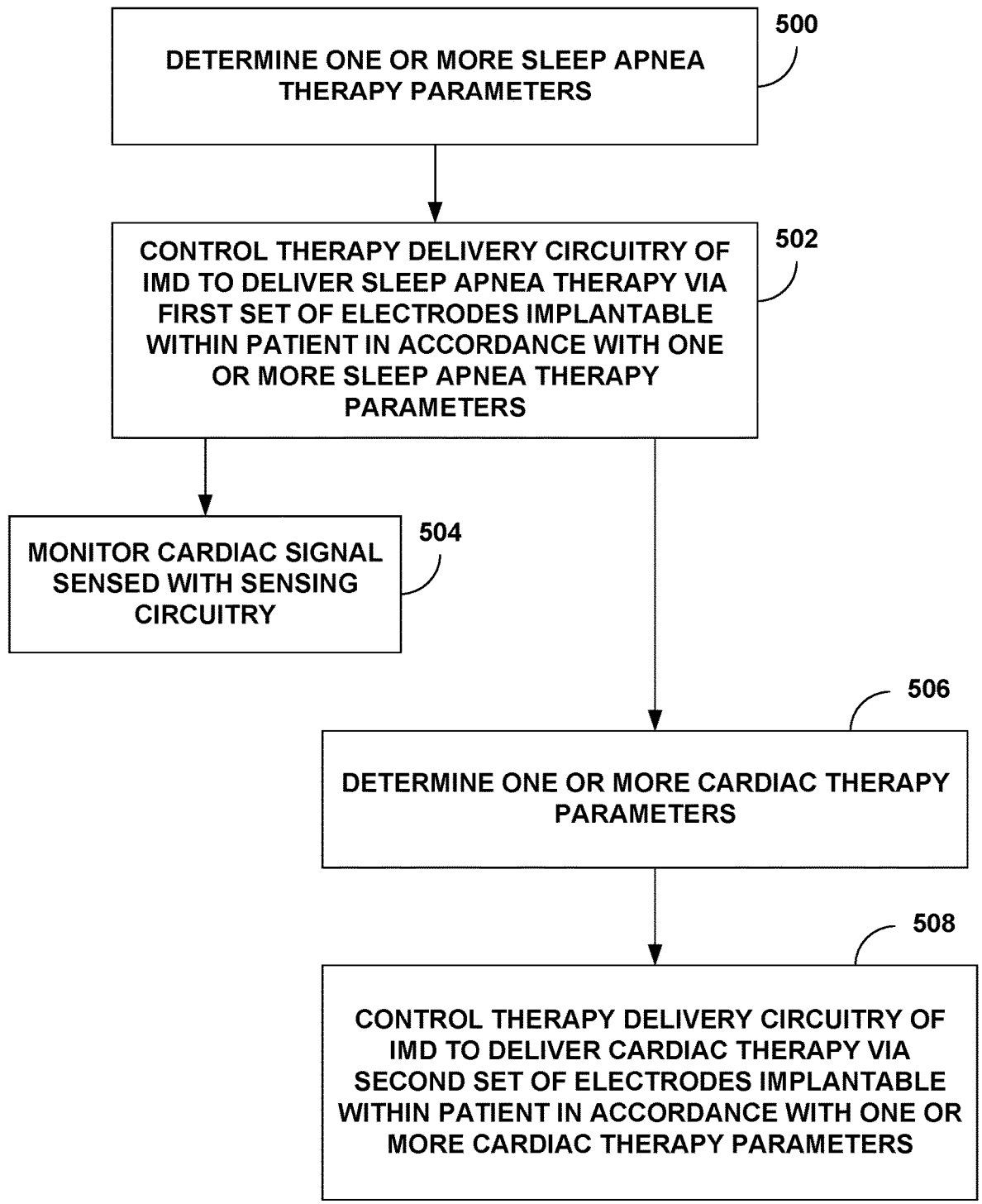
FIG. 5 is a flow diagram of an example method for delivering sleep apnea therapy and at least one of cardiac therapy or cardiac monitoring with an IMD.

FIG. 5 is a flow diagram of an example method for delivering sleep apnea therapy and at least one of cardiac therapy or cardiac monitoring with an IMD. For example, processing circuitry 302 or 400 may be configured to determine sleep apnea therapy parameters (500). Examples of sleep apnea therapy parameters, such as for OSA, are provided above, but the example techniques should not be considered so limiting. The sleep apnea therapy parameters may be for example sleep apnea therapy such as one or more of obstructive sleep apnea (OSA) therapy, central sleep apnea (CSA) therapy, and mixed apnea therapy (e.g., treating OSA and CSA simultaneously). Examples of the OSA therapy include anterior/posterior collapse therapy, and medial/lateral collapse therapy.

Processing circuitry 302 or 400 may control therapy delivery circuitry 306 of IMD 106 to deliver sleep apnea therapy via a first set of electrodes (e.g., electrodes 202 or electrodes on lead 126) implantable within patient 102 in accordance with the one or more sleep apnea therapy parameters (502). For example, controlling therapy delivery circuitry 306 to deliver the sleep apnea therapy may include processing circuitry 302 or 400 causing therapy delivery circuitry 306 to deliver the sleep apnea therapy to motor points of one or both hypoglossal nerves via the first set of electrodes. As another example, controlling therapy delivery circuitry 306 to deliver the sleep apnea therapy may include processing circuitry 302 or 400 causing therapy delivery circuitry 306 to deliver the sleep apnea therapy to a phrenic nerve via the first set of electrodes.

In one or more examples, processing circuitry 302 may be configured to monitor a cardiac signal sensed with sensing circuitry 304 (504). For example, to monitor the cardiac signal, processing circuitry 302 may detect a cardiac event when the cardiac electrical signal crosses a sensing threshold. The cardiac event detection circuitry may include a rectifier, filter and/or amplifier, a sense amplifier, comparator, and/or analog-to-digital converter. In general, processing circuitry 302 may monitor the cardiac signal to generation information indicative of a cardiac condition. Processing circuitry 302 may monitor the cardiac signal sensed with sensing circuitry 304 to determine HRV or detect arrhythmias such as atrial tachyarrhythmias and ventricular arrythmias, or more generally detect a cardiac condition including heart failure, possibility of sudden death or epilepsy.

In some examples, in addition to or instead of monitoring cardiac signal sensed with sensing circuitry 304, processing circuitry 302 may determine one or more cardiac therapy parameters (506). Examples of the cardiac therapy parameters, such as for ATP, are provided above, but the example techniques should not be considered so limiting. The cardiac therapy parameters may be for examples of cardiac therapy such as one or more of defibrillation therapy, cardiac resynchronization therapy (CRT), bradycardia therapy, and arrhythmia therapy.

Processing circuitry 302 or 400 may determine the one or more cardiac therapy parameters in response to sensing a condition associated with the sleep apnea therapy. As another example, processing circuitry 302 may determine the cardiac therapy parameters by receiving the cardiac therapy parameters from external device 108. As another example, processing circuitry 302 may determine the cardiac therapy parameters by retrieving the cardiac therapy parameters from memory 314. As another example, processing circuitry 400 may determine the cardiac therapy parameters based on clinician, patient 102, or caregiver input through user interface 404.

Processing circuitry 302 or 400 may control therapy delivery circuitry 306 of IMD 106 to deliver cardiac therapy via a second set of electrodes (e.g., electrodes 116, 118, 120, and 122) implantable within patient 102 in accordance with the cardiac therapy parameters (508). Second set of electrodes being electrodes 116, 118, 120, and 122 is one example. In some examples, processing circuitry 302 or 400 may control therapy delivery circuitry 306 to deliver the cardiac therapy via one or more leads that are configured to be implanted extravasculary and the second set of electrodes that are configured to be implanted extravasculary.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete logic circuitry, or other processing circuitry, as well as any combinations of such components, remote servers, remote client devices, or other devices. The term "processor" or "processing circuitry" may refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components. For example, any module described herein may include electrical circuitry configured to perform the features attributed to that particular module, such as fixed function processing circuitry, programmable processing circuitry, or combinations thereof.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that may, over time, change (e.g., in RAM or cache).

The following examples are illustrative of the techniques described herein.

Example 1. An implantable medical device (IMD), the IMD comprising: therapy delivery circuitry; sensing circuitry; and processing circuitry configured to: determine one or more sleep apnea therapy parameters; control the therapy delivery circuitry to deliver sleep apnea therapy via a first set of electrodes implantable within the patient in accordance with the one or more sleep apnea therapy parameters; and at least one of: (1) monitor a cardiac signal sensed with the sensing circuitry; or (2) determine one or more cardiac therapy parameters, and control the therapy delivery circuitry to deliver cardiac therapy via a second set of electrodes implantable within the patient in accordance with the one or more cardiac therapy parameters.

Example 2. The IMD of example 1, wherein the cardiac therapy includes one or more of defibrillation therapy, cardiac resynchronization therapy (CRT), bradycardia therapy, and arrhythmia therapy.

Example 3. The IMD of any of examples 1 and 2, wherein the sleep apnea therapy includes one or more of obstructive sleep apnea (OSA) therapy, central sleep apnea (CSA) therapy, and mixed apnea therapy.

Example 4. The IMD of any of examples 1-3, wherein the therapy delivery circuitry is configured to deliver the cardiac therapy via one or more leads that are configured to be implanted extravasculary and the second set of electrodes that are configured to be implanted extravasculary.

Example 5. The IMD of any of examples 1-4, wherein the therapy delivery circuitry is configured to deliver the sleep apnea therapy to at least one of: motor points of one or both hypoglossal nerves; and a phrenic nerve.

Example 6. The IMD of any of examples 1-5, wherein the processing circuitry is configured to determine the cardiac therapy parameters in response to sensing a condition associated with the sleep apnea therapy.

Example 7. The IMD of any of examples 1-6, wherein the processing circuitry is configured to determine the sleep apnea therapy parameters based on the monitored cardiac signal.

Example 8. The IMD of any of examples 1-7, wherein to determine the one or more cardiac therapy parameters and the one or more sleep apnea therapy parameters, the processing circuitry is configured to receive the one or more cardiac therapy parameters and the one or more sleep apnea therapy parameters from an external device.

Example 9. The IMD of any of examples 1-7, wherein to determine the one or more cardiac therapy parameters and the one or more sleep apnea therapy parameters, the processing circuitry is configured to retrieve the one or more cardiac therapy parameters and the one or more sleep apnea therapy parameters from memory.

Example 10. The IMD of any of examples 1-9, wherein the therapy delivery circuitry includes one of: common circuitry to deliver the cardiac therapy and the sleep apnea therapy; or cardiac therapy delivery circuitry configured to deliver the cardiac therapy and sleep apnea therapy delivery circuitry configured to deliver the sleep apnea therapy.

Example 11. A method of controlling therapy, the method comprising: determining one or more sleep apnea therapy parameters; controlling a therapy delivery circuitry to deliver sleep apnea therapy via a first set of electrodes implantable within a patient in accordance with the one or more sleep apnea therapy parameters; and at least one of: (1) monitoring a cardiac signal sensed with sensing circuitry; or (2) determining one or more cardiac therapy parameters, and controlling the therapy delivery circuitry to deliver cardiac therapy via a second set of electrodes implantable within the patient in accordance with the one or more cardiac therapy parameters.

Example 12. The method of example 11, wherein the cardiac therapy includes one or more of defibrillation therapy, cardiac resynchronization therapy (CRT), bradycardia therapy, and arrhythmia therapy.

Example 13. The method of any of examples 11 and 12, wherein the sleep apnea therapy includes one or more of obstructive sleep apnea (OSA) therapy, central sleep apnea (CSA) therapy, and mixed apnea therapy.

Example 14. The method of any of examples 11-13, wherein controlling the therapy delivery circuitry to deliver the cardiac therapy comprises causing the therapy delivery circuitry to deliver the cardiac therapy via one or more leads that are configured to be implanted extravasculary and the second set of electrodes that are configured to be implanted extravasculary.

Example 15. The method of any of examples 11-14, wherein controlling the therapy delivery circuitry to deliver the sleep apnea therapy comprises causing the therapy delivery circuitry to deliver the sleep apnea therapy to at least one of: motor points of one or both hypoglossal nerves; and a phrenic nerve.

Example 16. The method of any of examples 11-15, wherein determining the cardiac therapy parameters comprises determining the cardiac therapy parameters in response to sensing a condition associated with the sleep apnea therapy.

Example 17. The method of any of examples 11-16, wherein determining the sleep apnea therapy parameters comprises determining the sleep apnea therapy parameters based on the monitored cardiac signal.

Example 18. The method of any of examples 11-17, wherein determining the one or more cardiac therapy parameters and the one or more sleep apnea therapy parameters comprises receiving the one or more cardiac therapy parameters and the one or more sleep apnea therapy parameters from an external device.

Example 19. The method of any of examples 11-17, wherein determining the one or more cardiac therapy parameters and the one or more sleep apnea therapy parameters comprises retrieving the one or more cardiac therapy parameters and the one or more sleep apnea therapy parameters from memory.

Example 20. A computer-readable storage medium storing instructions thereon that when executed cause one or more processors to: determine one or more sleep apnea therapy parameters; control a therapy delivery circuitry to deliver sleep apnea therapy via a first set of electrodes implantable within a patient in accordance with the one or more sleep apnea therapy parameters; and at least one of: (1) monitor a cardiac signal sensed with sensing circuitry; or (2) determine one or more cardiac therapy parameters, and control the therapy delivery circuitry to deliver cardiac therapy via a second set of electrodes implantable within the patient in accordance with the one or more cardiac therapy parameters.

Example 21. The computer-readable storage medium of example 20, wherein the cardiac therapy includes one or more of defibrillation therapy, cardiac resynchronization therapy (CRT), bradycardia therapy, and arrhythmia therapy.

Example 22. The computer-readable storage medium of any of examples 20 and 21, wherein the sleep apnea therapy includes one or more of obstructive sleep apnea (OSA) therapy, central sleep apnea (CSA) therapy, and mixed apnea therapy.

Example 23. The computer-readable storage medium of any of examples 20-22, wherein the instructions that cause the one or more processors to control the therapy delivery circuitry to deliver the cardiac therapy comprise instructions that cause the one or more processors to cause the therapy delivery circuitry to deliver the cardiac therapy via one or more leads that are configured to be implanted extravascularly and the second set of electrodes that are configured to be implanted extravascularly.

Example 24. The computer-readable storage medium of any of examples 20-23, wherein the instructions that cause the one or more processors to control the therapy delivery circuitry to deliver the sleep apnea therapy comprise instructions that cause the one or more processors to cause the therapy delivery circuitry to deliver the sleep apnea therapy to at least one of: motor points of one or both hypoglossal nerves; and a phrenic nerve.

Example 25. The computer-readable storage medium of any of examples 20-24, wherein the instructions that cause the one or more processors to determine the cardiac therapy parameters comprise instructions that cause the one or more processors to determine the cardiac therapy parameters in response to sensing a condition associated with the sleep apnea therapy.

Example 26. The computer-readable storage medium of any of examples 20-25, wherein the instructions that cause the one or more processors to determine the sleep apnea therapy parameters comprise instructions that cause the one or more processors to determine the sleep apnea therapy parameters based on the monitored cardiac signal.

Example 27. The computer-readable storage medium of any of examples 20-26, wherein the instructions that cause the one or more processors to determine the one or more cardiac therapy parameters and the one or more sleep apnea therapy parameters comprise instructions that cause the one or more processors to receive the one or more cardiac therapy parameters and the one or more sleep apnea therapy parameters from an external device.

Example 28. The computer-readable storage medium of any of examples 20-26, wherein the instructions that cause the one or more processors to determine the one or more cardiac therapy parameters and the one or more sleep apnea therapy parameters comprise instructions that cause the one or more processors to retrieve the one or more cardiac therapy parameters and the one or more sleep apnea therapy parameters from memory.

Example 29. An implantable medical device (IMD), the IMD comprising: means for determining one or more sleep apnea therapy parameters; means for controlling a therapy delivery circuitry to deliver sleep apnea therapy via a first set of electrodes implantable within a patient in accordance with the one or more sleep apnea therapy parameters; and at least one of: (1) means for monitoring a cardiac signal sensed with sensing circuitry; or (2) means for determining one or more cardiac therapy parameters, and means for controlling the therapy delivery circuitry to deliver cardiac therapy via a second set of electrodes implantable within the patient in accordance with the one or more cardiac therapy parameters.

Example 30. The IMD of example 25, further comprising means for performing the method of any of examples 12-19.

Various examples have been described herein. Any combination of the described operations or functions is contemplated. These and other examples are within the scope of the following claims.

What is claimed is:

1. An implantable medical device (IMD), the IMD comprising:
therapy delivery circuitry;
sensing circuitry; and
processing circuitry configured to:
determine one or more sleep apnea therapy parameters;
control the therapy delivery circuitry to deliver sleep apnea therapy via a first set of electrodes implantable within a patient in accordance with the one or more sleep apnea therapy parameters;

determine a condition associated with the sleep apnea based on sensing via the sensing circuitry, wherein the condition comprises a low tone of a tongue of the patient or an apneic episode of the patient;

determine one or more cardiac therapy parameters in response to determination of the condition; and control the therapy delivery circuitry to deliver cardiac therapy via a second set of electrodes implantable within the patient in accordance with the one or more cardiac therapy parameters.

2. The IMD of claim 1, wherein the cardiac therapy includes one or more of defibrillation therapy, cardiac resynchronization therapy (CRT), bradycardia therapy, and arrhythmia therapy.

3. The IMD of claim 1, wherein the sleep apnea therapy includes one or more of obstructive sleep apnea (OSA) therapy, central sleep apnea (CSA) therapy, and mixed apnea therapy.

4. The IMD of claim 1, wherein the therapy delivery circuitry is configured to deliver the cardiac therapy via one or more leads that are configured to be implanted extravascularly and the second set of electrodes that are configured to be implanted extravascularly.

5. The IMD of claim 1, wherein the therapy delivery circuitry is configured to deliver the sleep apnea therapy to at least one of:
motor points of one or both hypoglossal nerves; and
a phrenic nerve.

6. The IMD of claim 1, wherein the processing circuitry is configured to determine the sleep apnea therapy parameters based on monitored cardiac signal.

7. The IMD of claim 1, wherein the therapy delivery circuitry includes one of:
common circuitry to deliver the cardiac therapy and the sleep apnea therapy; or
cardiac therapy delivery circuitry configured to deliver the cardiac therapy and sleep apnea therapy delivery circuitry configured to deliver the sleep apnea therapy.

8. A method of controlling therapy, the method comprising:
determining one or more sleep apnea therapy parameters;
controlling a therapy delivery circuitry to deliver sleep apnea therapy via a first set of electrodes implantable within a patient in accordance with the one or more sleep apnea therapy parameters;
determining a condition associated with the sleep apnea based on sensing via sensing circuitry, wherein the condition comprises a low tone of a tongue of the patient or an apneic episode of the patient;
determining one or more cardiac therapy parameters in response to determination of the condition; and
controlling the therapy delivery circuitry to deliver cardiac therapy via a second set of electrodes implantable within the patient in accordance with the one or more cardiac therapy parameters.

9. The method of claim 8, wherein the cardiac therapy includes one or more of defibrillation therapy, cardiac resynchronization therapy (CRT), bradycardia therapy, and arrhythmia therapy.

10. The method of claim 8, wherein the sleep apnea therapy includes one or more of obstructive sleep apnea (OSA) therapy, central sleep apnea (CSA) therapy, and mixed apnea therapy.

11. The method of claim 8, wherein controlling the therapy delivery circuitry to deliver the cardiac therapy comprises causing the therapy delivery circuitry to deliver the cardiac therapy via one or more leads that are configured to be implanted extravascularly and the second set of electrodes that are configured to be implanted extravascularly.

12. The method of claim 8, wherein controlling the therapy delivery circuitry to deliver the sleep apnea therapy comprises causing the therapy delivery circuitry to deliver the sleep apnea therapy to at least one of:
motor points of one or both hypoglossal nerves; and
a phrenic nerve.

13. The method of claim 8, wherein determining the sleep apnea therapy parameters comprises determining the sleep apnea therapy parameters based on monitored cardiac signal.

14. A non-transitory computer-readable storage medium storing instructions thereon that when executed cause one or more processors to:
determine one or more sleep apnea therapy parameters;
control a therapy delivery circuitry to deliver sleep apnea therapy via a first set of electrodes implantable within a patient in accordance with the one or more sleep apnea therapy parameters;
determining a condition associated with the sleep apnea based on sensing via the sensing circuitry, wherein the condition comprises a low tone of a tongue of the patient or an apneic episode of the patient;
determine one or more cardiac therapy parameters in response to determination of the condition; and
control the therapy delivery circuitry to deliver cardiac therapy via a second set of electrodes implantable within the patient in accordance with the one or more cardiac therapy parameters.

* * * * *